United States Patent
Tsuchida et al.

(10) Patent No.: US 7,618,658 B2
(45) Date of Patent: Nov. 17, 2009

(54) ANTI-MICROBIAL AGENT AND ANTI-MICROBIAL COMPOSITION

(75) Inventors: Yuuzou Tsuchida, Tokyo (JP); Kotarou Tsuchida, Tokyo (JP); Kenjirou Tsuchida, Tokyo (JP); Kunitomo Watanabe, Gifu (JP); Yoshiko Nakamura, Sagamihara (JP); Atsuo Iwasawa, Yokohama (JP)

(73) Assignee: Hououdou Co., Ltd., Tokyo (JP)

( * ) Notice: Subject to any disclaimer, the term of this patent is extended or adjusted under 35 U.S.C. 154(b) by 88 days.

(21) Appl. No.: 11/009,442

(22) Filed: Dec. 13, 2004

(65) Prior Publication Data

US 2005/0244515 A1 Nov. 3, 2005

Related U.S. Application Data

(63) Continuation of application No. PCT/JP03/07557, filed on Jun. 13, 2003.

(30) Foreign Application Priority Data

| Jun. 13, 2002 | (JP) | ............................. 2002-173214 |
| Dec. 4, 2002 | (JP) | ............................. 2002-352662 |
| May 6, 2003 | (JP) | ............................. 2003-128196 |

(51) Int. Cl.
 *A61K 36/899* (2006.01)
 *A01N 25/34* (2006.01)

(52) U.S. Cl. ........................................ 424/725; 424/404

(58) Field of Classification Search .................... None
See application file for complete search history.

(56) References Cited

U.S. PATENT DOCUMENTS

| 4,865,855 | A | * | 9/1989 | Hansen et al. |
| 6,034,133 | A | | 3/2000 | Hendley |
| 6,133,317 | A | | 10/2000 | Hart |
| 6,537,933 | B1 | * | 3/2003 | Tsuchida |
| 2006/0029627 | A1 | | 2/2006 | Tsuchida et al. |
| 2006/0251752 | A1 | | 11/2006 | Tsuchida et al. |
| 2008/0014292 | A1 | | 1/2008 | Tsuchida et al. |
| 2008/0131535 | A1 | | 6/2008 | Tsuchida et al. |

FOREIGN PATENT DOCUMENTS

| JP | 3-47118 | | 2/1991 | |
| JP | 4-49242 | | 2/1992 | |
| JP | 05007453 | A * | 1/1993 | |
| JP | 09176090 | A * | 7/1997 | |
| JP | 2000342236 | A2 * | 7/1997 | |
| JP | 9-255519 | | 9/1997 | |
| JP | 9-266765 | | 10/1997 | |
| JP | 11199502 | A * | 7/1999 | |
| JP | 2000-044419 | A | 2/2000 | |
| JP | 2001151655 | A * | 6/2001 | |
| JP | 2002-238524 | A | 8/2002 | |
| JP | 2000342236 | A2 * | 12/2002 | |
| JP | 2003-012494 | A | 1/2003 | |
| WO | WO 9918790 | * | 4/1999 | |
| WO | WO 9918970 | * | 4/1999 | |
| WO | WO 9962444 | A1 * | 12/1999 | |
| WO | WO 02/07745 | A1 | 1/2002 | |

OTHER PUBLICATIONS

Shimizu, T. Journal of the Food Hygienic Society of Japan, 1995; 36(1): 50-54. Antibacterial activity of several organic acids commonly used as food additives. Abstract.*
Conner, D. E. et al. Applied and Environmental Microbiology, 1995; 61(1):382-5. Growth and survival of *Escherichia coli* O157:H7.*
Kondo, I. et al. International Journal of Medical Microbiology, Sep. 2001; 201, No. Supplement 31, p. 13. Extract from bamboo grass kills *Helicobacter pylori*, revealing the coli structure of flagellar sheath.*
Lai Chungen, et al., "Chemical Composition of the Leaf-extracts of *Indocalamus*", Journal of Zhejiang Forestry College, www.cnki.net, 12(2), 1995, pp. 161-165 (with English Abstract).
Van Chuyen, et al., "Antimicrobial Activity of Kumaza ( *Sasa albomarginata*)," *Agric. Biol. Chem.* 46(4):971-978 (1982).
Kondo, et al., "Effects of Sasa Extract on Growth of *Staphylococcus aureus* and Various Types of Phages for *Staphylococcus*," *Bulletin of Bacteriological Society of Japan* 55(2):341 (2000).
Lai Chungen, et al., "Chemical Composition of the Leaf-extracts of Indocalamus", Journal of Zhejiang Forestry College. www.cnki.net, 12(2), 1995, pp. 161-165 (with English Abstract).
U.S. Appl. No. 11/484,679, filing date Jul. 12, 2006, Tsuchida, et al.
U.S. Appl. No. 11/009,442, filing date Dec. 13, 2004, Tsuchida, et al.
U.S. Appl. No. 11/249,387, filing date Oct. 14, 2005, Tsuchida, et al.
U.S. Appl. No. 11/246,194, filing date Oct. 11, 2005, Tsuchida, et al.
U.S. Appl. No. 11/009,442, filing date Oct. 14, 2005, Tsuchida, et al.

* cited by examiner

*Primary Examiner*—Michele Flood
(74) *Attorney, Agent, or Firm*—Sughrue Mion, PLLC

(57) ABSTRACT

A method for inhibiting growth of a *Staphylococcus aureus*, *Propionibacterium*, and *Escherichia coli* comprises the steps of providing an anti-microbial agent comprising *Sasa* tannin and contacting the microorganism to the anti-microbial agent.

7 Claims, No Drawings

ANTI-MICROBIAL AGENT AND ANTI-MICROBIAL COMPOSITION

TECHNICAL FIELD

The present invention relates to an anti-microbial agent containing a *Sasa* extract and more specifically to anti-*Clostridium tetani* agent, an anti-fungal agent, an anti-viral agent and an anti-microbial composition, which comprise a *Sasa* extract.

BACKGROUND ART

It has long been known that the *Sasa* extract shows an anti-microbial activity. For instance, there have been reported anti-microbial effects thereof on *Staphylococcus aureus, Pseudomonas aeruginosa* and *Escherichia coli* which are causative bacteria of wound-infectious diseases as well as anti-microbial effects thereof on *Helicobacter pylori* as the causative bacteria of gastric ulcers.

Sporangial and asporogenic anaerobes serving as causative bacteria of tetanus, gas gangrene and a variety of purulent infectious diseases cannot be disregarded as causative bacteria of wound-infectious diseases, but there has not yet been conducted any investigation of the anti-microbial activities for these anaerobes.

In the evaluation of substances having anti-microbial actions, it would be quite important to recognize the effects of such substances on useful and opportunistic bacteria which are settling in the skin and mucosae as parasitic bacteria, in addition to the effects thereof on the human pathogenic bacteria.

Incidentally, *Lactobacllus* spp. has been known as a parasitic bacterium settling in the oral cavity, digestive tract and vagina. In this respect, it has been well-known that the parasitic bacteria have two-sided actions on the living body. The *Lactobacllus* spp. is likewise sometimes isolated from clinical materials including blood and therefore, the effect thereof on the living body from the pathogenic aspect must not be underestimated. However, the frequency of the same isolated from such materials is quite low and therefore, it has been considered as a highly useful bacterial species in each particular anatomical site. For this reason, it is quite interesting to recognize or evaluate the magnitude of the anti-microbial effect of a *Sasa* extract on the *Lactobacllus* spp. which has been considered to be a bacterial group highly useful for the human being, but there has not yet been reported any detailed investigation thereof.

Incidentally, *Propionibacterium acnes* which settles in the sebaceous gland of the skin is an asporogenic anaerobic bacterium and it has been known as an exacerbation factor of *acne vulgaris* together with *Staphylococcus aureus* and *Staphylococcus epidermidis* in medium and serious cases of this disease. At the present time, there have been used a cream or a lotion containing an anti-microbial agent (such as erythromycin, tetracycline, nadifloxacin) in the treatment of the *acne vulgaris*, but the conversion of *Staphylococcus* spp. and *P. acnes* are converted into bacteria having resistance to these agents when using these agents over a long period of time and this becomes a clinical problem and accordingly, there has been discussed about measures against these resistant bacteria in the world-wide scale. There has not yet been reported any investigation of the effects of *Sasa* extracts on *P. acnes*.

*Prevotella bivia* and Pigmented *Prevotella* spp. are present in the vaginae of the healthy females only in the cell count lower than the detection limit, but they are obligatory anaerobic gram-negative *bacilli* which can undergo abnormal proliferation under the conditions of bacterial vaginosis (BV) characterized by the reduction of cell count of lactic acid bacteria present in the vagina, the reduction of the pH value in the vagina and leucorrhea having a milk-like appearance and giving out a bad smell (an amine-like smell) and which accordingly belong to the category of bacterial vaginosis (BV)-related microorganisms, together with anaerobic gram-positive *cocci* including, for instance, *Mycoplasma genitalium (hommnis), Gardnerella vaginalis* and *Peptostreptococcus anaerobius* as representatives, as well as *Porphyromonas* spp. and they are quite important bacteria as the causative bacteria of infectious diseases in the uterus and basin.

It has been known that the *Sasa* extract shows an anti-microbial action, but there has not yet been conducted any investigation of the anti-microbial action of the *Sasa* extract on these bacterial species belonging to the BV-related bacterial group.

As has been discussed above, it has not been known whether the *Sasa* extract shows the anti-microbial activity effective for the entire bacteria and it has not generally been known whether the extracts derived from naturally-occurring substances having anti-microbial activities on bacteria likewise show anti-microbial activities even on the mold such as *Candida*.

On the other hand, the tetanus is a toxin-induced disease showing a high lethality, in which a wound site is infected with *Clostridium tetani* and the neurotoxin produced at that site mainly causes muscle cramp, muscular rigidity and the accentuation of tendon reflex. The *Clostridium tetani* is an anaerobic bacillus detected in the soil, and feces of human beings and animals and it has been recognized that the tetanus can effectively be treated and/or prevented by the auto-immunization with toxoid or the passive immunization with an anti-venom serum. However, it has not yet been known that the *Sasa* extract has an anti-microbial activity against the *Clostridium tetani*.

Moreover, the virus is a quite fine pathogen which cannot undergo auto-growth, but can undergo parasitic growth in animals, plants or microorganisms and viruses can be divided into animal viruses, plant viruses and microbial viruses. There have been developed a variety of anti-viral agents for treating and/or preventing viral diseases, but there has still been desired for the development of agents having efficient anti-viral activities and free of any side effect.

Further, it has been known that tannin included in various kinds of plants shows anti-microbial activity. For instance, it is also well-known that tannin derived from plants other than *Sasa* has an anti-microbial activity against MRSA (mesitylene-resistant *Staphylococcus aureus*), but a problem arises such that the tannin cannot be used as an anti-microbial agent because of its serious side effect.

DISCLOSURE OF THE INVENTION

Accordingly, it is an object of the present invention to provide an anti-microbial agent and more specifically to provide an anti-tetanic agent, an anti-fungal agent and an anti-viral agent.

It is another object of the present invention to provide an anti-microbial composition.

According to the present invention, there are thus provided the following anti-microbial agent and anti-microbial composition:

1. An anti-tetanic agent comprising a *Sasa* extract.
2. An anti-fungal agent comprising a *Sasa* extract.

3. The anti-fungal agent as set forth in the foregoing item 2, wherein it farther comprises an organic acid.
4. The anti-fungal agent as set forth in the foregoing item 3, wherein the mold or fungus is *Candida*.
5. An anti-viral agent comprising a *Sasa* extract.
6. An anti-microbial agent comprising *Sasa* tannin.
7. The anti-microbial agent as set forth in the foregoing item 6, wherein it has an anti-microbial activity against *Staphylococcus aureus, Propionibacterium*, and *Escherichia coli*.
8. The anti-microbial agent as set forth in the foregoing item 6, wherein it has an anti-microbial activity against MRSA.
9. The anti-microbial agent as set forth in the foregoing item 6, wherein it has an anti-microbial activity against *Propionibacterium acnes*.
10. An agent for treating acne comprising *Sasa* tannin.
11. An anti-microbial composition comprising a *Sasa* extract and an organic acid.
12. The anti-microbial composition as set forth in the foregoing item 11, wherein the composition is an ink, a paint, a food additive, a beverage, a seasoning, a pet food, a plastic molded article or an additive.
13. An anti-microbial agent against gas gangrene-causative bacteria comprising a *Sasa* extract.
14. The anti-microbial agent as set forth in the foregoing item 13, wherein the gas gangrene-causative bacteria are those belonging to genus *Clostridium*.
15. An anti-microbial agent against asporogenic anaerobic gram-positive *cocci* comprising a *Sasa* extract.
16. The anti-microbial agent as set forth in the foregoing item 15, wherein the asporogenic anaerobic gram-positive coccus is *Finegoldia, Micromonas, Peptostreptococcus, Atopobium*, or *Gemella*.
17. An anti-microbial agent against asporogenic anaerobic gram-negative *bacilli* comprising a *Sasa* extract.
18. The anti-microbial agent as set forth in the foregoing item 17, wherein the asporogenic anaerobic gram-negative bacillus is *Prevotella, Porphyromonas, Bilophila, Desulfovivrio* or *Fusobacterium*.
19. An anti-microbial agent against vaginitis-related and bacterial vaginosis-related microorganisms comprising a *Sasa* extract.
20. The anti-microbial agent as set forth in any one of the foregoing items 13 to 19, wherein it further comprises an organic acid.
21. A seasoning comprising a *Sasa* extract.
22. The seasoning of the foregoing item 21, wherein it is common salt containing a *Sasa* extract.
23. The seasoning of the foregoing item 21 or 22, wherein it further comprises an organic acid.
24. An agricultural chemical comprising a *Sasa* extract.
25. The agricultural chemical of the foregoing item 24, wherein it further comprises an organic acid.
26. An agricultural disinfectant comprising a *Sasa* extract.
27. The agricultural disinfectant of the foregoing item 26, wherein it further comprises an organic acid.
28. A preservative comprising a *Sasa* extract.
29. The preservative of the foregoing item 28, wherein it further comprises an organic add.

In this respect, agents such as an anti-tetanic agent, an anti-fungal agent, an anti-viral agent and an acne-treating agent will sometimes generically be referred to as "anti-microbial agent" in this specification.

Moreover, the term "anti-microbial agent" herein used includes those used for not only human beings but also animals other than human beings and preservatives as well.

BEST MODE FOR CARRYING OUT THE INVENTION

The present invention relates to an anti-microbial agent comprising a *Sasa* extract as an effective component. The anti-microbial agent according to the present invention comprises the *Sasa* extract in an amount ranging from 1 to 50% by mass, preferably 2 to 25% by mass and more preferably 4 to 15% by mass as expressed in terms of the solid content thereof. This is because if the solid content of the *Sasa* extract present in the agent is less than 1% by mass, the resulting anti-microbial agent shows insufficient anti-microbial activity, while if it exceeds 50% by mass, the resulting anti-microbial agent has an extremely high irritating action for the affected site or the like.

Conventionally, the *Sasa* extract has been prepared in the form of an extract generally containing the solid content thereof in an amount of 0.5 to 10% by mass and used in a variety of applications. The extract having such a solid content is in general used in an amount of 1 to 10% by mass on the basis of the mass of the final product and therefore, the solid content of the *Sasa* extract present in the final product is in general in the order of about 0.05 to 0.8% by mass. In other words, the solid content in the final product is, at highest, less than about 1% by mass. The reason for this is, for instance, that the *Sasa* extract is relatively expensive, that the *Sasa* extract shows its anti-inflammatory effect or its anti-microbial effect, to some extent, even at such a low concentration and that it is not practical to increase the added amount of the effective component to a level of not less than 10% by mass. In most of cases, however, the final product having such a low concentration of the effective component simply shows an insufficient anti-microbial effect.

The inventors of this invention have found that if the *Sasa* extract is incorporated into an anti-microbial agent in an amount ranging from 1 to 10% by mass, preferably 2 to 8% by mass and more preferably 3 to 7% by mass as expressed in terms of the solid content thereof, the resulting product or the anti-microbial agent shows an effect of improving, for instance, atopy, and a conspicuous antipruritic effect, which have never been achieved by the use of the *Sasa* extract at such a conventional low concentration and the resulting product further shows a considerably improved wound-healing effect (WO 02/07745). The inventors of this invention have further inquired into the anti-microbial activities of the *Sasa* extract against a variety of bacteria, fungi and/or viruses and have found that if the *Sasa* extract is added to an anti-microbial agent in an amount ranging from 1 to 50% by mass, preferably 2 to 25% by mass and more preferably 4 to 15% by mass as expressed in terms of the solid content thereof, the resulting anti-microbial agent shows a conspicuous anti-microbial activity against bacteria other than *Staphylococcus aureus, Pseudomonas aeruginosa* and *Escherichia coli* and more specifically, anaerobic bacteria such as *Clostridium tetani, Propionibacterium* including *Propionibacterium acnes*, fungi such as *Candida*, or viruses such as herpes virus, influenza virus, corona virus and that the incorporation of an organic acid such as malic acid into the *Sasa* extract would permit the considerable improvement of the anti-microbial activity thereof and the inventors have thus completed the present invention. There has not conventionally been reported any attempt to use the *Sasa* extract in a high concentration, although the *Sasa* extract per se has long been known, but the reason for this has not yet been clearly elucidated. Surprisingly, however, the *Sasa* extract having a solid content or concentration higher than that conventionally used (not less than 10 times) shows significant anti-microbial activities even against anaerobic bacteria such as *Clostridium tetan*, fungi such as *Candida*, or viruses.

The present invention is likewise effective for the infectious diseases of dermal soft tissues. When the skin, bone, soft tissues are damaged due to a trauma, ischemia or surgical operations, an environment is established, which is quite susceptible to the infection with anaerobic bacteria. The infectious diseases of dermal soft tissues are apt to occur at sites, which are susceptible to the contamination with feces and/or the exudates from the upper respiratory tract. Examples of such sites are wound parts related to the operations of intestinal tracts, decubitus, and the trauma related to a bite by a man. The anaerobic bacteria are isolated from cases or patients suffering from crepitant cellulites, synergistic cellulites, gangrene and necrotic fascitis, which are accompanied by the generation of gases. Moreover, the anaerobic bacteria are likewise isolated from patients suffering from dermal abscess, rectal abscess and infectious diseases of axillary sudoriferous gland (purulent hidradenitis). The anaerobic bacteria are also frequently isolated from the ankle ulcers of diabetics.

The infectious diseases of dermal soft tissues are in general those caused by a plurality of bacteria (mixed infection). In this respect, about 4.8 kinds of bacteria are, on the average, isolated per case and the ratio of the anaerobic bacteria to the aerobic ones is found to be 3:2. Examples of bacterial strains isolated at a high frequency include *Bacteroides* spp., *Peptostreptococcus* spp., *Enterococcus* spp., *Clostridium* spp. and *Proteus* spp. When these anaerobic bacteria take part in such infectious diseases, the probability of causing fever increases, the affected part may give out a bad smell, a gas is generated in the affected tissues and ulcers may be formed on feet.

The gangrene originated from the synergistic actions of the anaerobic bacteria and facultative bacteria (Meleney's gangrene) is characterized by the severe pain, rubefaction, and swelling, as well as the induration generated subsequent thereto. The red spots (or erythema) spread around the necrosed region as a center. A granular ulcer is growing at the central portion as the red spots and gangrene outwardly spread. A pain is an only symptom thereof and the generation of heat or fever is not a typical symptom thereof. This infectious disease is caused, in most of cases, due to the combined action of *S. aureus* and *Peptostreptococcus* spp. The sites quite susceptible to the infection of this disease are operated wounds in the abdominal regions and peripheral regions around ulcers on the leg (or lower extremity). The methods for treating the same are the surgical removal of necrosed tissues and anti-microbial chemotherapy.

The necrotic fascitis or a destructive disease of the fascia, which may rapidly spread over a wide region, is caused, in most of cases, due to the infection with the group A streptococci, but it may sometimes be caused by the infection with an anaerobic bacterium such as *Peptostreptococcus* or *Bacteroides*. In some cases, a gas-generation phenomenon is observed in the affected tissues. Similar to this, the muscular necrosis relates to the mixed infection with anaerobic bacteria and facultative bacteria. Fournier gangrene is one of the crepitant cellulites in which a plurality of anaerobic bacteria invading or damaging the scrota, the perineal region, and the fore part of the abdominal wall may spread along the deep external facial planes to thus result in a wide spread of dermal defects.

The present invention herein provides an agent for treating and/or preventing the infectious diseases of the dermal soft tissues, which comprises a *Sasa* extract.

The present invention also relates to an anti-microbial agent having an anti-microbial activity against *Propionibacterium* including *Propionibacterium acnes*.

The inventors of this invention have conducted further investigation of the effective components present in the *Sasa* extract, have found that tannin included therein in a relatively large amount shows an excellent anti-microbial activity and have thus completed the present invention. It has conventionally been reported that tannins have anti-microbial activities, but it has been known that none of them is not put into practical use because of their severe side effects. It has been known that the *Sasa* extract per se has long been orally ingested and is free of any side effect on the human body. However, it has unexpectedly been found that tannins are included in such a *Sasa* extract in a relatively high content and they show excellent anti-microbial activities.

The *Sasa* (*Sasa albo-marginata*) used in the present invention, as a raw material for the *Sasa* extract is not restricted to any specific one and any plant belonging to the genus *Sasa* may be used herein. Specific examples thereof include those specified below: Kumai *Sasa; Sasa albo-marginata* Makino et Shibata (Kuma *Sasa*); ground bamboo; Okuyama *Sasa*; Ezo-Miyama *Sasa; Sasa Paniculata* Makino et Shibata; Yahiko *Sasa*; Oba *Sasa*; Miyama *Sasa*; Sendai *Sasa*; Yukawa *Sasa*; Aboi *Sasa*; and Onuka *Sasa*. Among these, specific examples of commercially available ones include Kumai *Sasa* and Kuma *Sasa* (Chugoku *Sasa* and Hida *Sasa*). For instance, preferably used herein are extracts derived from, for instance, Kumai *Sasa* and/or Kuma *Sasa* collected in, for instance, TESHIO Mountains in Hokkaido, Japan during the term extending from July to October.

The *Sasa* extract used in the present invention is preferably one prepared by extracting raw leaves or dried leaves of *Sasa*, preferably dried leaves thereof with water maintained at a temperature ranging from 100 to 180° C. at ordinary pressure or while applying a pressure.

The extraction method is not restricted to any particular one, but usable herein includes, for instance, that disclosed in Japanese Patent No. 3,212,278 (Japanese Un-Examined Patent Publication Hei 11-196818). More specifically, leaves of *Sasa albo-marginata* are extracted at a temperature ranging from 100 to 180° C. for 5 to 30 minutes using a pressurized hot water extraction device, the resulting extract is separated from a moisture-containing solid content (moisture content: 40 to 70%) in a moisture separator, thereafter the moisture-containing solid content is treated at a temperature ranging from 100 to 200° C. for 5 to 60 minutes in a saturated vapor-heating device, the solid content thus treated is again treated at 100 to 180° C. for 5 to 30 minutes using a pressurized hot water extraction device and the extracts obtained in the first and second extraction steps are combined prior to practical use. Alternatively, it is also possible to use an extract obtained by extracting dried leaves of *Sasa albo-marginata* with, for instance, water heated to 60 to 100° C. for 30 minutes to 12. hours.

There have been known "AHSS" available from Chloroland Moshiri Co., Ltd. and "TWEBS" available from HOUOUDOU Co., Ltd. as examples of commercially available ones having a content of the *Sasa* extract of 50% by mass as expressed in terms of the solid content of the extract.

The *Sasa* extract thus obtained contains sulfur-containing components and the content thereof as expressed in terms of the amount of sulfur ranges from about 4 to 10 mg and usually about 6 to 9 mg per one gram of the solid content of the *Sasa* extract. Principal constituents of the sulfur-containing components are considered to be sulfur containing amino acids.

The anti-microbial agent according to the present invention comprises such sulfur-containing components derived from the *Sasa* extract in an amount preferably ranging from 4 to 500 mg, more preferably 8 to 250 mg and most preferably 16 to 150 mg per 100 g of the composition, as expressed in terms of the amount of sulfur.

Moreover, the *Sasa* extract contains tannins and the content thereof in the solid contents is in the order of about 5 to 15% by mass based on the total mass of the solid contents.

It is desirable that the anti-microbial agent according to the present invention comprise the tannins derived from the *Sasa* extract in an amount preferably ranging from 0.05 to 7.5% by mass and more preferably 0.1 to 6% by mass as expressed in terms of the concentration of the solid contents of the extract.

The anti-microbial agent according to the present invention may comprise only the *Sasa* extract as an effective component or the simultaneous use of a reasonable amount of an organic acid would permit the further improvement of the anti microbial activity of the resulting agent. Examples of such organic acids include malic acid, citric acid, lactic acid, oxalic acid, malonic acid, succinic acid, fumaric acid, acetic acid, benzoic acid, phenyl-acetic acid, salicylic acid and phenols.

The amount of such an organic acid used in the anti-microbial agent according to the present invention preferably ranges from 0.01 to 5% by mass, more preferably 0.02 to 3% by mass and most preferably 0.05 to 1.5% by mass based on the total mass of the anti-microbial agent.

The anti-microbial agent of the present invention may be the *Sasa* extract per se or a combination of the *Sasa* extract, other components and a carrier.

The present invention further provides a seasoning such as common salt, sugar, soy sauce, miso, sauce, mayonnaise, sake, sweet sake (mirin) and dressings, which comprises a mixture of the *Sasa* extract and an organic acid For instance, if the *Sasa* extract or a mixture of the *Sasa* extract with an organic acid is added to common salt, the resulting common salt has an effect such that the resulting common salt can considerably extend the shelf life of, for instance, fishes and meat. The amount of the *Sasa* extract to be added to common salt preferably ranges from 1 to 10% by mass, more preferably 2 to 8% by mass and most preferably 3 to 6% by mass as expressed in terms of the solid content of the extract.

The anti-microbial agent of the present invention may be in any form such as a liquid, a solid or a gas. The anti-microbial agent of the present invention may be administered through an oral or parenteral route. Examples of dosage forms administered through the oral route are a tablet, a pill, a powder, a liquid preparation, and a food such as a chewing gum, wheat gluten, chocolate, bred, cookies, buckwheat noodles, wheat vermicelli, and various kinds of beverages; and examples of dosage forms administered through the parenteral route are an injection, locally administered agents (such as a cream and an ointment) and a suppository. Examples of dosage forms of such locally administered agents are those obtained by impregnating absorbent gauze made of natural fibers or synthetic fibers with the anti-microbial agent of the present invention and cosmetic products such as lipsticks or rouge to which the anti-microbial agent of the present invention is added.

The anti-microbial agent of the present invention is not only effective for the human being, but also effective as an anti-microbial agent for the mammals other than man, the birds, fishes and the reptiles. Therefore, the anti-microbial agent of the present invention may be used as an anti-bacterial agent for these animals (such as a pharmaceutical agent for pets and a pet food). Moreover, the anti-microbial agent of the present invention may likewise be useful as an anti-bacterial agent for a variety of plants in addition to animals and may also be effective as an antiseptic.

To prepare the anti-microbial agent of the present invention in a variety of dosage forms, it is possible to use, for instance, a base component such as oily components used in, for instance, the usual pharmaceutical compositions, cosmetics, and compositions externally applied to the skin; a humectant; and an antiseptic.

The water used in the antimicrobial agent is not particularly restricted and may be tap water, natural water, and purified water, but preferably used herein are in general highly purified water such as ion-exchanged water.

Examples of such oily components are animal oils such as squalane, tallow, lard, horse fat, lanolin and yellow bees wax; plant's oils such as olive oil, grape seed oil, palm oil, jojoba oil and germ oil (such as rice germ oil); and synthetic or semi-synthetic oils such as liquid paraffin, higher fatty acid esters (such as octyl paimitate, isopropyl palmitate, octyl dodecyl myristate) and silicone oil.

The oily components are appropriately combined so as to satisfy the requirements for characteristics such as the skin-protection effect, an emollient effect (an effect of covering the skin surface with a thin film to thus prevent drying of the skin and to impart softness and elasticity to the skin) and refreshed feeling. An example of such a combination preferably used herein comprises squalane, olive oil and octyl dodecyl myristate.

The anti-microbial agent may further comprise a solid oil such as stearic acid, stearyl alcohol, behenic acid, cetanol, and vaseline, with the combination of stearic acid and cetanol being preferably used.

When the anti-microbial agent of the present invention is prepared in the form of a cream composition, a creaming agent is used for converting the *Sasa* extract, water and oily components into a cream-like product. Such a creaming agent is not restricted to any particular one, but it is common to use glyceryl monostearate and a self-emulsifying glyceryl monostearate in combination (a product obtained by the addition of an emulsifying agent to glyceryl monostearate).

The anti-microbial agent of the present invention may further comprise, if necessary, a stabilizer, a humectant, a wound-healing agent, an antiseptic and/or a surfactant.

Examples of such stabilizers are a combination of a carboxy vinyl polymer with potassium hydroxide, and polyethylene glycol di-stearate. Particularly preferably used herein is polyethylene glycol sesqui-stearate (a 1:1 mixture of polyethylene glycol di-stearate with polyethylene glycol monostearate; molecular weight of the polyethylene glycol: 1000 to 20,000) since the stability thereof is high, it is never separated into aqueous and oil phases and the resulting cream composition has a hardness, upon the application thereof to the skin, which can effectively be controlled.

Examples of the foregoing humectants are sodium hyaluronate, collagen, aloe extract (in particular, the aloe extract (2) derived from *A. arborescens* Mill. var. *natalensis* Berg), urea, 1,3-butylene glycol, glycerin, trehalose, sorbitol, amino acids and sodium pyrrolidone carboxylate.

Examples of the foregoing wound-healing agents are allantoin, di-potassium glycyrrhizinate, glycyrrhiza extract and the extract derived from *Artemisia princeps* Pamp.

The foregoing antiseptics are used as a supplementary since the *Sasa* extract shows an anti-microbial activity in itself. Examples of such antiseptics include sodium benzoate, lower alkyl esters of p-hydroxy benzoic acid (those commonly known as parabens such as methyl, ethyl, propyl and butyl esters thereof, sodium propionate, mixed fatty acid esters (a mixture of glyceryl caprylate, lauric acid polyglyceryl-2 and lauric acid polyglyceryl-10), phenoxy ethanol, photosensitizer No. 201 (yellow dyestuff) and 1,2-pentanediol, with parabens, mixed fatty acid esters and 1,2-pentanediol being preferably used herein.

Examples of surfactants usable herein are sodium N-acyl-L-glutamate and polyoxyethylene sorbitan monostearate.

The anti-microbial agent of the present invention may further include, if necessary, a component capable of emitting fragrance such as orange oil, lemon oil, bitter orange peel oil, and perfumes.

Water and, if necessary, an organic acid are added to the foregoing ingredients to thus make the total amount of the resulting agent 100% by mass.

The following Table 1 shows the preferred relative amount (% by mass) of individual components used when preparing the anti-microbial agent of the present invention in the form of a cream composition. The amount of each component other than water corresponds to that (% by mass) of the component free of any moisture.

TABLE 1

| Component | Preferred Range | More preferred range | Most preferred range |
| --- | --- | --- | --- |
| Sasa extract | 1 to 50 | 2 to 25 | 4 to 15 |
| Liquid oily component | 6 to 30 | 2 to 20 | 5 to 15 |
| Solid oily component | 2 to 35 | 3 to 25 | 5 to 15 |
| Creaming agent | 1 to 6 | 1.5 to 4 | 1.6 to 3 |
| Stabilizer | 0 to 2 | 0 to 1.5 | 0 to 1 |
| Humectant | 0 to 10 | 0.05 to 5 | 0.1 to 5 |
| Wound-healing agent | 0 to 2 | 0.05 to 1 | 0.1 to 0.5 |
| Flavor | 0 to 5 | 0 to 3 | 0 to 1 |
| Organic acid | 0.01 to 5 | 0.1 to 3 | 0.5 to 1.5 |
| Water | Balance | Balance | Balance |

The foregoing components are introduced into a heat-mixing kettle equipped with a stirring blade and an emulsifier, followed by mixing these components with stirring at a temperature ranging from 70 to 90° C. for 1 to 2 hours to thus give an anti-microbial agent of the present invention.

In addition to the foregoing cream composition, the anti-microbial agent of the present invention can likewise be used in the form of, for instance, an ointment, a liquid, a jelly, a gel and aerosol, but the agent is most preferably used in the form of a cream composition since the cream can easily be used and shows a high level of its desired effect. The anti-microbial agent may also be used in the form of a semi-solid or a liquid such as a shampoo, a body soap and a cleansing foam.

It would be desirable that the anti-microbial agent of the present invention be applied to the affected part in an appropriate amount, for instance, in an amount ranging from about 0.1 to 1 g per 100 cm$^2$ of the skin, 1 to 5 times a day and usually 1 to 3 times a day, when it is used in the form of, for instance, a cream composition, after cleaning the affected part. The amount of the agent to be applied and the frequency of the application thereof may be adjusted while taking into consideration each particular symptom and the extent of each wound.

On the other hand, when the anti-microbial agent of the present invention is orally ingested, it is desirable that the agent be ingested in an amount ranging from 0.01 to 0.1 g/kg body weight as expressed in terms of the solid content of the Sasa extract, 1 to 5 times a day and usually 1 to 3 times a day. The amount of the agent to be ingested and the frequency of the ingestion thereof may be adjusted while talking into consideration each particular symptom.

When the anti-microbial agent of the present invention is administered through a parenteral route, in the form of, for instance, a parenteral injection, it is desirable that the agent be administered in an amount ranging from 0.01 to 0.1 g/kg body weight as expressed in terms of the solid content of the Sasa extract, 1 to 5 times a day and usually 1 to 3 times a day. The amount of the agent to be administered and the frequency of the administration thereof may be adjusted while taking into consideration each particular symptom.

The anti-microbial agent of the present invention can be coated on, for instance, a condom to thus prevent the infection with, for instance, venereal diseases and HIV infectious diseases.

The Sasa extract as an effective component of the anti-microbial agent of the present invention is an extract derived from plants belonging to the genus Sasa and a 1.25% by mass aqueous solution thereof never shows any toxicity to 293 cells derived from the fetal kidney.

The anti-microbial agent of the present invention comprises the Sasa extract in an amount ranging from 1 to 50% by mass as expressed in terms of the solid content thereof and shows significant anti-microbial activity against a variety of microorganisms such as Clostridium tetani, gas gangrene-causative bacteria belonging to the genus Clostridium, which are accompanied by gas gangrene, bacteria belonging to the genus Candida, Trichophyton, Mucor, Rhizopus, bacteria belonging to the genus Aspergillus, bacteria belonging to the genus Cryptococcus, bacteria belonging to the genus Coccidioides, bacteria belonging to the genus Human Plasma, antibiotic-resistant bacteria such as MRSA, bacteria belonging to the genus Propionibacterium including Propionibacterium acnes, and viruses such as herpes virus, influenza virus and corona virus.

The following are preferred embodiments of the anti-microbial agent according to the present invention:

1. An anti-microbial agent comprising a Sasa extract (1 to 50% by mass as expressed in terms of the solid content thereof), water, an oily component and a creaming agent.
2. The anti-microbial agent of the foregoing item 1, wherein the oily component is at least one member selected from the group consisting of animal oils, plant's oils, synthetic oils and semi-synthetic oils.
3. The anti-microbial agent of the foregoing item 1, wherein the oily component is at least one member selected from the group consisting of squalane, tallow, lard, horse fat, lanolin, yellow bees wax, olive oil, grape seed oil, palm oil, jojoba oil, germ oil, liquid paraffin, octyl palmitate, isopropyl palmitate, octyl dodecyl myristate, silicone oil, stearic acid, stearyl alcohol, behenic acid, cetanol and vaseline.
4. The anti-microbial agent as set forth in any one of the foregoing items 1 to 3, wherein the creaming agent is a combination of glyceryl monostearate and a self-emulsifying glyceryl monostearate.
5. The anti-microbial agent as set forth in any one of the foregoing items 1 to 3, wherein it further comprises at least one member selected from the group consisting of stabilizers, humectants, wound-healing agents, antiseptics and surfactants.
6. The anti-microbial agent of the foregoing item 5, wherein the stabilizer is at least one member selected from the group consisting of a combination of a carboxy vinyl polymer with potassium hydroxide, and polyethylene glycol di-stearate.
7. The anti-microbial agent of the foregoing item 5, wherein the humectant is at least one member selected from the group consisting of sodium hyaluronate, collagen, aloe extract, urea, 1,3-butylene glycol, glycerin, trehalose, sorbitol, amino acids and sodium pyrrolidone carboxylate.

8. The anti-microbial agent of the foregoing item 5, wherein the wound-healing agent is at least one member selected from the group consisting of allantoin, di-potassium glycyrrhizinate, glycyrrhiza extract and the extract derived from *Artemisia princeps* Pamp.

9. The anti-microbial agent of the foregoing item 5, wherein the antiseptic is at least one member selected from the group consisting of sodium benzoate, lower alkyl esters of p-hydroxy benzoic acid, sodium propionate, mixed fatty acid esters, phenoxy ethanol, 1,2-pentanediol and yellow dyestuff.

10. The anti-microbial agent of the foregoing item 5, wherein it further comprises at least one member selected from the group consisting of orange oil, lemon oil, bitter orange peel oil, and perfumes.

11. An anti-microbial agent which comprises a *Sasa* extract, water, an oily component, a creaming agent, a stabilizer, a humectant, a wound-healing agent, an antiseptic and a surfactant, wherein the oily component is at least one member selected from the group consisting of squalane, tallow, lard, horse fat, lanolin, yellow bees wax, olive oil, grape seed oil, palm oil, jojoba oil, germ oil, liquid paraffin, octyl palmitate, isopropyl palmitate, octyl dodecyl myristate, silicone oil, stearic acid, stearyl alcohol, behenic add, cetanol and vaseline; the creaming agent is a combination of glyceryl monostearate and a self-emulsifying glyceryl monostearate; the stabilizer is at least one member selected from the group consisting of a combination of a carboxy vinyl polymer with potassium hydroxide, and polyethylene glycol di-stearate; the humectant is at least one member selected from the group consisting of sodium hyaluronate, collagen, aloe extract, urea, 1,3-butylene glycol, glycerin, trehalose, sorbitol, amino acids and sodium pyrrolidone carboxylate; the wound-healing agent is at least one member selected from the group consisting of allantoin, di-potassium glycyrrhizinate, glycyrrhiza extract and the extract derived from *Artemisia princeps* Pamp.; the antiseptic is at least one member selected from the group consisting of sodium benzoate, lower alkyl esters of p-hydroxy benzoic acid, sodium propionate, mixed fatty acid esters, phenoxy ethanol and yellow dyestuff, and the surfactant is sodium N-acyl-L-glutamate.

12. The anti-microbial agent of the foregoing item 11, wherein it further comprises at least one member selected from the group consisting of orange oil, lemon oil, bitter orange peel oil, and perfumes.

13. The anti-microbial agent of the foregoing item 1, wherein it comprises a *Sasa* extract, water, squalane, olive oil, glyceryl monostearate, self-emulsifying glyceryl monostearate, carboxy vinyl polymer, potassium hydroxide, urea, 1,3-butylene glycol, allantoin, a lower alkyl ester of p-hydroxy benzoic acid, stearic acid, sodium N-acyl-L-glutamate and lemon oil.

14. The anti-microbial agent of the foregoing item 1, wherein it comprises a *Sasa* extract, water, squalane, olive oil, octyl dodecyl myristate, cetanol, glyceryl monostearate, self-emulsifying glyceryl monostearate, carboxy vinyl polymer, potassium hydroxide, urea, 1,3-butylene glycol, allantoin, mixed fatty acid ester, stearic acid, sodium N-acyl-L-glutamate and orange oil.

15. The anti-microbial agent as set forth in any one of the foregoing items 1 to 14, wherein it comprises polyethylene glycol sesqui-stearate.

16. The anti-microbial agent as set forth in any one of the foregoing items 1 to 15, wherein the organic acid is at least one member selected from the group consisting of malic acid citric acid, lactic acid, oxalic acid, malonic acid, succinic acid, fumaric acid, acetic acid, benzoic acid, phenylacetic acid, salicylic acid and phenols.

The present invention also provides an anti-microbial composition which comprises a *Sasa* extract and an organic acid. Preferred embodiments of the anti-microbial composition according to the present invention are, for instance, an ink, a coating or paint, a food additive, a beverage, a pet food, a plastic molded article and an adhesive.

When using, as a raw material for these anti-microbial compositions, an aqueous raw material such as a food additive, a beverage (for instance, a refreshing beverage, a fruit juice, a vegetable juice and an alcoholic drink (such as sake, beer, a sparkling alcoholic beverage, whisky, a low-class distilled spirit, vodka, wine and brandy)), it is sufficient for the preparation of each corresponding anti-microbial composition that the *Sasa* extract and an organic acid are added to and/or admixed with these raw materials. The *Sasa* extract and the organic acid may be added thereto in any stage and more specifically prior to, during and/or after the preparation of a particular raw material. After the addition of the *Sasa* extract and the organic acid, these ingredients are mixed together, with stirring, at a temperature ranging from 70 to 90° C. for 1 to 2 hours to thus further improve the anti-microbial activity of the resulting composition. The content of the *Sasa* extract present in the anti-microbial composition such as a food additive or a beverage preferably ranges from 0.1 to 20% by mass and more preferably 0.25 to 7% by mass.

Alternatively, when using, for instance, ink, a coating, a plastic molded article or an adhesive, as such a raw material for the anti-microbial composition and if these raw materials are hydrophilic, it is sufficient for the preparation of each corresponding anti-microbial composition that the *Sasa* extract and an organic acid are added to and/or admixed with these raw materials, as has already been discussed above. The *Sasa* extract and the organic acid may be added thereto in any stage and more specifically prior to, during and/or after the preparation of a particular raw material. On the other hand, if these raw materials are hydrophobic (or lipophilic), the *Sasa* extract and the organic acid are not miscible with these raw materials in most of cases. Thus, it is desirable to improve the miscibility of these two components with an individual raw material by taking measures, for instance, by the simultaneous use of the *Sasa* extract or a mixture of the *Sasa* extract and an organic acid with a surfactant (an emulsifying agent) or a hydrophilic organic solvent (for instance, an alcohol such as methyl alcohol and ethyl alcohol; a ketone such as acetone; an ester such as ethyl acetate; pyridine; and/or dimethylformamide); or by the preliminary encapsulation of the *Sasa* extract or a mixture of the *Sasa* extract and an organic acid using a lipophilic material. In any case, after the addition of the *Sasa* extract and the organic acid, these ingredients are mixed together, with stirring, at a temperature ranging from 70 to 90° C. for 1 to 2 hours to thus further improve the anti-microbial activity of the resulting composition.

When using, for instance, an ink, a coating, a plastic molded article or an adhesive, as such a raw material for the anti-microbial composition of the present invention, the content of the *Sasa* extract in the composition preferably ranges from 1 to 20% by mass and more preferably 3 to 7% by mass, while the content of the organic acid therein preferably ranges from 0.1 to 10% by mass and more preferably 3 to 7% by mass.

Organic acids particularly preferably used herein are, for instance, malic acid, succinic acid and citric acid.

The anti-microbial composition of the present invention shows a significant anti-microbial activity as compared with any composition free of the anti-microbial agent of the present invention and the composition such as ink or a coating is quite useful, as an anti-microbial construction material not only for the ordinary family, but also for hospitals in which there is a danger of the hospital acquired infection as well as a construction material for public buildings.

The present invention will further be described below in more detail with reference to the following Reference Examples, Examples and Test Examples.

REFERENCE EXAMPLE 1

Preparation of *Sasa* Extract

Dried leaves of the *Sasa albo-marginata* collected in TESHIO Mountains in Hokkaido Japan in September were introduced into a pressurized hot water extraction tank, treated at 125° C. for 10 minutes in the tank, the hot water was cooled down to about 80° C. by the action of a cooling water and then the resulting extract was separated from the moisture-containing solid content using a screw-press in such a manner that the moisture content of the latter was controlled to a level of about 50% by mass. Then the solid contents having a moisture content of about 50% by mass were introduced into an autoclave and heat-treated under pressure at 180° C. for 10 minutes using saturated steam. The moisture-containing solid contents thus treated were again introduced into a pressurized hot water-extraction tank and treated at 110° C. for 5 minutes to thus obtain an extract. The first and second extracts were combined together, filtered through a diatomaceous earth layer, the resulting filtrate was concentrated under reduced pressure till the solid content thereof was increased to 50% by mass and the concentrate thus prepared was subjected to a fluidized sterilization treatment at a temperature ranging from 110 to 130° C. to give a *Sasa* extract.

The *Sasa* extract thus prepared was inspected for the sulfur content and it was found to be 3850 μm/ml (7.7 mg per one gram of the solid content).

REFERENCE EXAMPLE 2

The commercially available *Sasa* extract (the extract derived from Bambuseae *Sasa*; available from HOUOUDOU Co., Ltd.) was inspected for the components thereof and as a result, the extract included the following components: Water: 59.5% by mass; Proteins: 8.6% by mass; Lipid: 0.6% by mass; Minerals: 9.0% by mass; Carbohydrates: 19.8% by mass; and Tannins: 2.5% by mass.

EXAMPLES 1 TO 4

The components listed in the following Table 2 were admixed together in amounts (% by mass) likewise specified in Table 2, introduced into a heating and mixing kettle equipped with a stirring blade and an emulsifier and then mixed therein with stirring at 80° C. for 2 hours to thus give each corresponding anti-microbial agents according to the present invention. The added amounts of a *Sasa* extract having a solid content of 8% by mass (a product obtained by diluting, with water, the *Sasa* extract having a solid content of 50% by mass and prepared in Reference Example 1) were 12.5, 25, 37.5 and 75% by mass respectively (therefore, the contents of the extract as expressed in terms of the solid content thereof were 1, 2, 3 and 6% by mass; and the sulfur contents of these samples were 7.7 mg, 15.4 mg, 23.1 mg and 46.2 mg per 100 g of the anti-microbial agents, respectively).

TABLE 2

| Component | Amount (% by mass) |
| --- | --- |
| Squalane | 5.0 |
| Olive oil | 6.0 |
| Lemon oil | 1.0 |
| Stearic acid | 4.0 |
| Glyceryl monostearate | 0.8 |
| Carboxy vinyl polymer (CARBOPOL 940) | 0.2 |
| Glyceryl monostearate (self-emulsifiable type one) | 1.0 |
| Sodium N-acyl-L-glutamate | 0.2 |
| 1,3-Butylene glycol | 1.0 |
| Urea | 10.0 |
| Allantoin | 0.1 |
| Methyl p-oxy-benzoate | 0.1 |
| Propyl p-oxy-benzoate | 0.1 |
| Sasa extract (solid content 8% by mass) | Desired amount |
| Potassium hydroxide | 0.02 |
| Ion-exchange water (to 100% by mass) | |

COMPARATIVE EXAMPLE 1

The same procedures used in Example 1 were repeated except for changing the added amount of the *Sasa* extract having a solid content of 8% by mass (a product obtained by diluting, with water, the *Sasa* extract having a solid content of 50% by mass and prepared in Reference Example 1) to 6.2% by mass (therefore, the content of the extract as expressed in terms of the solid content thereof was 0.5% by mass; and the sulfur content of the sample was 3.8 mg per 100 g of the anti-microbial agent) to thus give an anti-microbial agent of Comparative Example 1.

EXAMPLE 5

The same procedures used in Examples 1 to 4 were repeated using the components shown in the following Table 3 in the amounts (% by mass) likewise specified in Table 3 to thus give each corresponding anti-microbial agent according to the present invention.

TABLE 3

| Component | Amount (% by mass) |
| --- | --- |
| Squalane | 1.0 |
| Olive oil | 4.0 |
| Orange oil | 1.0 |
| Octyl dodecyl myristate | 6.0 |
| Stearic acid | 4.0 |
| Cetanol | 2.0 |
| Polyethylene glycol di-stearate | 0.5 |
| Glyceryl monostearate | 1.0 |
| Carboxy vinyl polymer (CARBOPOL 940) | 0.2 |
| Glyceryl monostearate (self-emulsifiable type one) | 1.4 |
| Sodium N-acyl-L-glutamate | 0.2 |
| 1,3-Butylene glycol | 1.0 |
| Urea | 3.0 |
| Allantoin | 0.1 |
| Mixed fatty acid ester (NIKOGUARD DL) | 0.5 |
| Sasa extract (solid content: 8% by mass) | 75.0 |
| Potassium hydroxide | 0.05 |
| Ion-exchange water (to 100% by mass) | 0.05 |

The resulting anti-microbial agent was found to have a sulfur content of 46.2 mg per 100 g thereof.

EXAMPLE 6

The components listed in the following Table 4 were admixed together in amounts (% by mass) likewise specified in Table 4, introduced into a heating and mixing kettle equipped with a stirring blade and an emulsifier and then mixed therein with stirring at 80° C. for 2 hours to thus give an anti-microbial agent according to the present invention.

TABLE 4

| Component | Amount (% by mass) |
| --- | --- |
| Liquid paraffin | 10.0 |
| Squalane | 1.0 |
| Olive oil | 1.0 |
| Orange oil | 1.0 |
| Octyl dodecyl myristate | 6.0 |
| 1,2-Pentanediol | 0.5 |
| Phenoxy-ethanol | 0.5 |
| Cetanol | 1.5 |
| Stearic acid | 4.0 |
| Glyceryl monostearate | 2.0 |
| Glyceryl monostearate (self-emulsifiable type one) | 2.5 |
| Polyethylene glycol di-stearate | 0.5 |
| Carboxy vinyl polymer | 0.3 |
| Sodium N-acyl-L-glutamate | 0.2 |
| 1,3-Butylene glycol | 1.0 |
| Ethanol | 3.0 |
| Tri-methyl glycine | 0.5 |
| Sodium hyaluronate | 1.0 |
| Sasa extract (solid content: 50% by mass) | 12.0 |
| Purified water | 51.5 |

The pH value of the resulting cream was found to be 6.00.

EXAMPLE 7

The components listed in the following Table 5 were admixed together in amounts (% by mass) likewise specified in Table 5, introduced into a heating and mixing kettle equipped with a stirring blade and an emulsifier and then mixed therein with stirring at 80° C. for 2 hours to thus give an anti-microbial agent according to the present invention.

TABLE 5

| Component | Amount (% by mass) |
| --- | --- |
| Olive oil | 3.0 |
| Squalane | 1.0 |
| Liquid paraffin | 3.0 |
| Cetanol | 1.3 |
| Glyceryl monostearate | 2.0 |
| Glyceryl monostearate (self-emulsifiable type one) | 5.0 |
| Polyoxyethylene (20) stearyl ether | 1.0 |
| Polyoxyethylene (20) cetyl ether | 1.0 |
| Polyoxyethylene (140) monostearate | 1.0 |
| Bentonite | 0.5 |
| Xanthane gum | 0.2 |
| Glucono-δ-lactone | 4.0 |
| dl-Malic acid | 1.0 |
| Triethanolamine | 3.3 |
| 1,2-Pentanediol | 0.5 |
| Phenoxy-ethanol | 0.5 |
| 1,3-Butylene glycol | 2.0 |
| Sasa extract (solid content: 50% by mass) | 12.0 |
| Purified water | 57.7 |

The pH value of the resulting cream was found to be 4.68.

EXAMPLE 8 TO 10

The same procedures used in Example 7 were repeated except that dl-malic acid was not added, that the amount of the *Sasa* extract (solid content: 50% by mass) used was changed to 16, 20 or 30% by mass and that the amount of the purified water was correspondingly and appropriately adjusted to thus give each corresponding anti-microbial agent in the form of a cream according to the present invention, which had a content of the *Sasa* extract (amount of the solid content thereof was 8, 10 or 15% by mass.

EXAMPLES 11 TO 13

The same procedures used in Example 7 were repeated except that the amount of the *Sasa* extract (solid content: 50% by mass) used was changed to 16, 20 or 30% by mass and that the amount of the purified water was correspondingly and appropriately adjusted to thus give each corresponding anti-microbial agent in the form of a cream according to the present invention, which had a content of the *Sasa* extract (amount of the solid content thereof) was 8, 10 or 15% by mass.

TEST EXAMPLE 1

Anti-microbial Activity against *Clostridium tetani*

In this Test Example, 26 strains of *Clostridium tetani* were used. These strains were isolated from the soil collected in Japan. As controls, there were used *Escherichia coli* (ATCC 25922) and *Staphylococcus aureus* (ATCC 25923) as well.

The *Sasa* extract prepared in Reference Example 1 (the content of *Sasa* extract's solid contents: 50% by mass) was diluted with sterilized, distilled water to give an aqueous *Sasa* extract solution.

The minimum growth-inhibitory concentration of the *Sasa* extract aqueous solution was determined using *Sasa* extract aqueous solutions having a variety of concentrations, according to the agar plate-dilution method. More specifically, variable GAM agar plates (available from NISSUI Pharmaceutical Co., Ltd.) were prepared such that the final concentrations of these plates were equal to 12.5, 6.25, 3.13, 1.56, 0.78, 0.39, 0.19 and 0.10% by mass, respectively. The *Sasa* extract aqueous solution and the two-fold diluted agar medium were admixed together at a mixing ratio of 1:1 to thus prepare each agar medium containing the *Sasa* extract at a predetermined concentration. In this respect, the concentration of the agar was corrected to 3% to prevent any migration of the bacterial cells of *Clostridium tetani*. The colony of the test strain obtained by cultivating it on the variable GAM agar plate whose agar concentration had been adjusted to 3% over 24 hours was scraped out with a platinum loop, suspended in Anaerobe broth (available from Difco) and then the turbidity thereof was adjusted to Mc Farland No. 0.5. Then a series of *Sasa* extract-containing plates were inoculated with the resulting suspension (1 μl; inoculum size: $10^5$ cfu) according to the streak-smearing method. Regarding the control strains, the colony of each control strain grown on a blood-agar medium was suspended in Anaerobe broth (available from Difco), the turbidity thereof was adjusted to Mc Farland No. 0.5 and then a series of *Sasa* extract-containing plates were inoculated with the resulting suspension (1 μl; inoculum size: $10^5$ cfu) according to the streak-smearing method. In this connection, these samples were cultivated at 35° C. for 18 hours in an anaerobic work station (available from GUNZE Industries, Inc.) and then the culture mediums were visually examined on whether each strain underwent growth or not. The case in which the strain underwent growth was judged to be positive (+).

The minimum inhibitory concentrations of the *Sasa* extract were determined for *Escherichia coli* (ATCC 25922) and *Staphylococcus aureus* (ATCC 25923) and both of them were found to be 3.13% by mass.

The minimum inhibitory concentrations of the *Sasa* extract observed for the 26 strains of *Clostridium tetani* were distributed within the range of from 0.19% by mass to 0.78% by mass. These. results are summarized in the following Table 6. The *Sasa* extract concentration required for inhibiting 80% of each *Clostridium tetani* strain used and that required for inhibiting 50% thereof (MIC80% and MIC50%) were found to be 0.78% and 0.39%, respectively.

TABLE 6

| Minimum Inhibitory Concentration (%) | No. of Strains |
|---|---|
| 12.5 | 0 |
| 6.25 | 0 |
| 3.15 | 0 |
| 1.56 | 0 |
| 0.78 | 11 |
| 0.39 | 14 |
| 0.19 | 1 |
| 0.10 | 0 |
| Total | 26 |

The tetanus is a disease originated from the invasion of the endospores of *Clostridium tetani* present in the soil into a wound site along with the soil. It is essential or indispensable to the crisis of this disease that the endospores undergo the germination and growth to thus produce a toxin (tetanospasmin). The contaminated wound site may be quite susceptible to the establishment of an anaerobic environment suitable for the germination of the endospores and therefore, the bases for the prevention of any crisis of the tetanus are to subject the contaminated wound site to an appropriate surgical treatment such as the removal of the invading foreign substances and necrosed tissues or the treatment called debridement in order to thus prevent the establishment of any anaerobic environment in the wound site and to prevent any growth of the *Clostridium tetani*.

As shown in Table 6, the *Sasa* extract completely inhibited the growth of the whole 26 strains of *Clostridium tetani* examined at such a low concentration of at highest 0.78% by mass. It has thus been proved that the anti-microbial activity of the *Sasa* extract is not less than 4 times that observed for *Escherichia coli* and *Staphylococcus aureus*.

In the microscopic observation of the *Clostridium tetani* obtained according to the simple staining method at a *Sasa* extract concentration (0.19%) at which the growth of the bacteria was identical to that observed when using a medium free of any *Sasa* extract, there were observed images of bacterial cells which were converted into filaments or got swollen and lysed. In addition, there were easily observed the presence of bacterial cells insufficient in the color-developing ability and bacterial cells having endospores, at a *Sasa* extract concentration (0.38%) which permitted the significant inhibition of the growth of the bacteria as compared with that observed when using a medium free of any *Sasa* extract. There have already been obtained, in the microscopic observation, the information which may suggest the inhibition of the septal wall-formation in the *Staphylococcus aureus*. It has been known from the studies of antibiotics that the conversion into filaments observed at a *Sasa* extract concentration of not more than the minimum inhibitory concentration thereof is a phenomenon observed when the septal wall-formation upon the cell division is inhibited.

It would be expected that the *Sasa* extract shows the anti-microbial activity against several anaerobic bacteria which may cause the gas gangrene as an external wound-related disease having a disease outbreak mechanism similar to that of the tetanus, or a group of gas gangrene-causative bacteria such as *Clostridium perfringens, Clostridium septicum* and *Clostridium bifermentans*, and the anti-microbial activity thereof against the asporogenic anaerobic bacteria as the causative bacteria of purulent infectious diseases.

TEST EXAMPLE 2

Examination of Anti-microbial Activity against *Candida*

The *Sasa* extracts and the cream compositions each containing the *Sasa* extract and an organic acid prepared in Examples 8 to 13 were inspected for the anti-microbial activities against a bacterium belonging to the genus *Candida* (*Candida albicans* as a clinically isolated strain).

Culture Medium:

NB Culture medium: The nutrient broth supplemented with 0.2% meat extract (available from EIKEN Chemical Co., Ltd.);

1/50 NB Culture medium: A product obtained by diluting the NB culture medium 50 times with a phosphate buffer solution to thus adjust the pH thereof to 7.2±0.2;

SCDLP bouillon (available from EIKEN Chemical Co., Ltd.);

SA Culture medium: Standard agar culture medium (available from NISSUI Pharmaceutical Co., Ltd.).

Preparation of Bacterial Solution

The freshly cultured bacterial cells obtained by the pure culture thereof before one day from the testing day are suspended in the 1/50 NB culture medium at a turbidity of Mc Farland No. 0.5 or a density of about $10^8$ cells/ml. Moreover, the resulting suspension or the bacterial solution is diluted 100 times with the 1/50 NB culture medium (about $10^6$ cells/ml).

The foregoing cream compositions are melted by heating the same at 60° C. for 10 minutes. Each of the melted cream compositions (1 ml) is dropped on an acrylic plate (50 mm×50 mm), followed by allowing to stand for 10 minutes at room temperature to thus solidify the composition. The bacterial solution (0.5 ml each) is dropwise added to the surface of the acrylic plate coated with the cream composition and then an acrylic plate (45 mm×45 mm) is closely adhered thereto. The resulting assembly is cultured at 36° C. for 24 hours, under a high humidity condition.

To a sterilized Petri dish, there is added 10 ml of the SCDLP bouillon and the acrylic plates cultivated over 24 hours are transferred to the bouillon to thus wash out the culture mediums on the acrylic plates into the bouillon. bouillon (100 μl ) is then taken from the wash liquid and dropwise added to the SA culture medium and uniformly spread over the medium, followed by the cultivation thereof over 48 hours, the determination of the viable count and the conversion thereof into the bacterial cell number per acrylic plate. The results thus obtained are listed in the following Table 7.

TABLE 7

| Test No. | Cream | Sasa extract | Malic acid | Immediately after the inoculation | After 24 hours |
|---|---|---|---|---|---|
| 1 | — | — | — | $1.7 \times 10^4$ | $9.6 \times 10^6$ |
| 2 | Control | — | — |  | $8.5 \times 10^5$ |
| 3 | Example 8 | 8% | — |  | $2.3 \times 10^5$ |
| 4 | Example 9 | 10% | — |  | $1.8 \times 10^5$ |
| 5 | Example 10 | 15% | — |  | — |
| 6 | Example 11 | 8% | 1% |  | $2.4 \times 10^5$ |
| 7 | Example 12 | 10% | 1% |  | $1.0 \times 10^3$ |
| 8 | Example 13 | 15% | 1% |  | $2.0 \times 10^2$ |

Control: The cream of Example 7 free of any dl-malic acid and Sasa extract.

The cream compositions comprising the *Sasa* extract, but free of any dl-malic acid (Test Nos. 3 to 5) show almost no anti-microbial activity against the bacterium belonging to the genus *Candida*, while the compositions comprising both the *Sasa* extract and dl-malic acid (Test Nos. 6 to 8) show high anti-microbial activities, in particular, at a *Sasa* extract concentration of not less than 10% by mass.

TEST EXAMPLE 3

Effect of Healing Herpes Virus-Induced Infectious Diseases

An appropriate amount of the cream composition (the amount of the solid contents present in the *Sasa* extract: 6% by mass) prepared in Example 7 was applied onto the affected part (a corner of the mouth) of a herpes virus-infected patient (60-year-old, female) twice a day and as a result, it was found that the symptom thereof was significantly relieved by the treatment over 2 days and the affected part was completely healed by the treatment over 3 days.

TEST EXAMPLE 4

Analysis of Strains Isolated from Lesions of Patients Suffering from Acne

There were isolated the following 44 strains of *Staphylococcus aureus* and 26 strains belonging to the genus *Propionibacterium acnes* from the lesions of a patient suffering from *acne*.

TABLE 8

| | |
|---|---|
| Staphylococcus epidermidis | 34 |
| Staphylococcus homminis | 1 |
| Staphylococcus capitis | 1 |
| Staphylococcus haemolyticus | 2 |
| Staphylococcus aureus | 2 |
| Staphylococcus cohnii | 1 |
| Others | 3 |
| Propionibacterium acnes | 26 |

The following are the sensitivities (μg/ml) of the foregoing 44 strains of *Staphylococcus aureus* to antibiotics:

TABLE 9

| Antibiotics | MIC Range | MIC 50 | MIC 90 |
|---|---|---|---|
| OFLX | 0.19~>100 | 0.39 | 0.78 |
| NDFX | 0.025~25 | 0.05 | 0.78 |
| TC | 0.19~>100 | 0.39 | 25 |
| MINO | 0.10~50 | 0.10 | 0.10 |
| CLDM | 0.025~>100 | 0.10 | >100 |

The following are the sensitivities (μg/ml) of the foregoing 26 strains belonging to the genus *Propionibacterium acnes* to antibiotics:

TABLE 10

| Antibiotics | MIC Range | MIC 50 | MIC 90 |
|---|---|---|---|
| OFLX | 0.39~0.78 | 0.39 | 0.39 |
| NDFX | 0.10~0.39 | 0.19 | 0.19 |
| TC | 0.19~1.56 | 0.19 | 0.19 |
| MINO | 0.05~0.39 | 0.05 | 0.39 |
| CLDM | 0.025~0.78 | 0.10 | 0.19 |

TEST EXAMPLE 5

Anti-microbial Activity of *Sasa* Extract of Reference Example 2

The *Sasa* extract *Sasa* tannin) prepared in Reference Example 2 and a commercially available tannin (Lot. 02060618, available from Extrasynthese, Geney, France) were inspected for the anti-microbial activities (MIC (mg/m): minimum inhibitory concentration), on an agar culture medium according to the two-fold dilution method. The results thus obtained are shown in the following Table.

TABLE 11

| Bacteria | Sasa Extract, MIC(mg/ml) | Tannin, MIC(mg/ml) |
|---|---|---|
| S. aureus ATCC25923 | 0.8~1.6 (0.05~0.1) | 0.02~0.04 |
| P. acnes PA-1 | 6.4 (0.4) | 0.08 |
| E. coli ATCC25922 | 1.6~3.2 (0.1~0.2) | >0.63 |

The numerical value in the parenthesis indicates the MIC value observed for the *Sasa* extract as expressed in terms of the *Sasa* tannin.

TEST EXAMPLE 6

Anti-microbial Activity of *Sasa* Extract of Reference Example 2

The *Sasa* extract (*Sasa* tannin) prepared in Reference Example 2 and a commercially available tannin (Lot. 02060618, available from Extrasynthese, Geney, France) were inspected for the anti microbial activities (MIC (mg/ml): minimum inhibitory concentration), on an agar culture medium according to the two-fold dilution method, using the 44 strains (mixture) belonging to the genus *Staphylococcus* and the 26 strains belonging to the genus *Propionibacterium acnes* isolated from the lesions of a patient suffering from acne as described in Test Example 4. The results thus obtained are shown in the following Table. The bacteria belonging to the genus *Staphylococcus* were cultivated on an MH agar (Mueller Hinton Agar (BBL)) culture medium having a pH value of 7.0, in the air at 37° C. for 24 hours, while those belonging to the genus *Propionibacterium acnes* were cultivated on a GAM culture medium having a pH value of 7.0, under an anaerobic condition at 35° C. for 48 hours. In this connection, the MIC80 values observed for the commercially available tannin were found to be 0.04 mg/ml for the bacterial group of the genus *Staphylococcus* and 0.08 mg/ml for that of the genus *Propionibacterium acnes*.

TABLE 12

| Bacteria | Sasa Extract | | | commercially available |
| --- | --- | --- | --- | --- |
| | MIC Range | MIC 50 | MIC 80 | tannin MIC 80 |
| Bacteria belonging to the genus *Staphylococcus* (44 strains) | 0.1~1.6 | 0.4 | 0.8 | 0.04 |
| Bacteria belonging to the genus *Propionibacterium acnes* (26 strains) | 3.2~6.4 | 6.4 | 6.4 | 0.08 |

EXAMPLE 4

To 100 parts by mass of an water-based ink, there were added 6 parts by mass of the *Sasa* extract prepared in Reference Example 1 and 10 parts by mass of dl-malic acid and then these components were mixed and heated at 80° C. for 2 hours to thus form an anti-microbial ink.

EXAMPLE 15

To 100 parts by mass of an water-based paint, there were added 6 parts by mass of the *Sasa* extract prepared in Reference Example 1 and 10 parts by mass of dl-malic acid and then these components were mixed and heated at 80° C. for 2 hours to thus form an anti-microbial paint.

EAXMPLE 16

To 100 parts by mass of Sake, there were added 3 parts by mass of the *Sasa* extract prepared in Reference Example 1 and 0.25 part by mass of dl-malic acid and then these components were mixed and heated at 80° C. for 3 hours to thus form an anti-microbial Sake.

EXAMPLE 17

To 100 parts by mass of an aqueous adhesive, there were added 6 parts by mass of the *Sasa* extract prepared in Reference Example 1 and 10 parts by mass of dl-malic acid and then these components were mixed and heated at 80° C. for 2 hours to thus form an anti-microbial adhesive.

EXAMPLE 7

Anti-microbial Activities against 10 Strains of Gas Gangrene-Causative Bacteria: *Clostridium perfringens*

Strains Used: There were used 10 strains in all comprising one strain of *C. perfringens* ATCC 13124 and clinically isolated 9 strains of *C. perfringens* (GAI-92099, GAI-92100, GAI-92101, GAI-92102, GAI-92103, GAI-92104, GAI-92105, GAI-92106 and GAI-92107). These clinically isolated strains are those isolated from clinical materials derived from patients infected with these bacteria and stored in *Anaerobic* Bacterial Experimental Facilities affiliated to the medical department of GIFU University (hereunder referred to as "the present Facilities"). In this respect, *E. coli* ATCC 25922 was used as the reference strain for the evaluation of the degree of anti-microbial activity (or for managing the precision of the evaluation).

The concentration of the solid contents present in the *Sasa* extract was found to be 50%. The solid contents comprise water-soluble proteins and amino acids, minerals, tannins, glucide, water-soluble polysaccharides, carboxylic acids, overall chlorophylls, silicic acid, vitamins, lipids, refined oils, and moisture. The pH value of the stock solution was about 5.0. Sterilized distilled water was used for the dilution of the solution.

Anti-microbial Activity Test: The minimum inhibitory concentration (%) of each sample was determined according to the agar plate dilution method used in the determination of the anti-microbial power of anti-microbial drugs. More specifically, a series of two-fold diluted aqueous solutions of *Sasa* extract were prepared such that the final concentration thereof fell within the range of from 25% to 0.2%. The *Sasa* extract aqueous solution and the variable GAM agar culture medium (two-fold) were admixed together at a mixing ratio of 1:1 to thus prepare each variable GAM agar culture medium containing the *Sasa* extract at a final concentration thereof ranging from 12.5 to 0.1%. The colony of the test strain obtained by cultivating it on the variable GAM agar culture medium over 24 hours was scraped out with a sterilized cotton swab and suspended in Anaerobe broth (available from Difco) to thus form a bacteria-containing solution having a turbidity of Mc Farland No. 1. Then a series of *Sasa* extract-containing plates were inoculated with the resulting suspension (10 μl; inoculum size: $10^6$ cfu) according to the streak-smearing method Regarding the control strains of *E. coli*, the colony formed on a TSA agar culture medium (available from Difco) was suspended in Anaerobe broth, the turbidity thereof was adjusted to Mc Farland No. 0.5 and then a series of *Sasa* extract-containing plates were inoculated with the resulting suspension (10 μl; inoculum size: $10^5$ cfu) according to the streak-smearing method. In this connection, these samples were cultivated at 35° C. for 18 hours in an anaerobic work station (available from GUNZE Industries, Inc.) and then the culture mediums were visually examined on whether each strain underwent growth or not. The case in which the strain underwent growth was judged to be positive (+). The minimum inhibitory concentrations of the *Sasa* extract were determined for *Escherichia coli* (ATCC 25922) and it was found to be 3.13%.

The minimum concentrations of the *Sasa* extract required for inhibiting the growth of the 10 strains of *C. perfringens* were found to be distributed within the range of from 3.13 to 6.25%. The *Sasa* extract concentration required for inhibiting 80% of the strains used and that required for inhibiting 50% thereof (MIC80% and MIC50%) were found to be 6.25%.

TABLE 13

Anti-microbial Action of Sasa Extract against 10 Strains of *Clostridium perfringens*

| Minimum Inhibitory Concn. Of Sasa Extract (%) | Number of Strains |
| --- | --- |
| 12.5 | 0 |
| 6.25 | 8 |
| 3.13 | 2 |
| 1.56 | 0 |
| 0.78 | 0 |
| 0.39 | 0 |
| 0.19 | 0 |
| 0.10 | 0 |
| Sum | 10 |

Consideration:

The gas gangrene is a disease originated from the invasion of the endospores of a group of *Clostridium* spp. referred to as gas gangrene-causative bacteria present in the soil into a wound site along with the soil. Examples of causative bacteria thereof conventionally known include *Clostridium perfringens, Clostridium septicum* and *Clostridium bifermentans* and 80% of the cases of such gas gangrene are caused by *C. perfringens*. It has been known that the gas gangrene is a disease which can sufficiently be prevented by an appropriate emergency surgical treatment, but if such a surgical treatment is late in the day, by any possibility or if such a surgical treatment is insufficient, one may be attacked with this disease on and after 6 hours from the instance when he is wounded, then the symptom thereof rapidly proceeds and the wound may thus be fatal. Moreover, the affected parts such as the legs and arms are obliged to cut off from the patient for the purpose of saving his life and therefore, this is one of the diseases which cannot treat lightly.

The results obtained in the foregoing in vitro tests clearly indicate that the anti-microbial activity of the *Sasa* extract against *C. perfringens* is inferior to that of the *Sasa* extract against *C. tetani* as the results obtained in Test Example 1, but the *Sasa* extract completely inhibited the 10 strains of *C. perfringens* at a concentration of not less than 3.13% and not more than 6.25%. Accordingly, the affected part-protecting cloth or the like impregnated with the *Sasa* extract would ensure the foregoing minimum inhibitory concentration for *C. perfringens* and therefore, when it is applied to, for instance, the human body as an emergency treatment after being injured and prior to any appropriate treatment by a surgeon, the *Sasa* extract would show its effect of inhibiting the germination of *C. perfringens* at the injured site or any growth of the bacterium after the germination thereof.

TEST EXAMPLE 8

Anti-microbial Activities of *Sasa* Extract against a Group of Gas Gangrene-Causative Bacteria other than *Clostridium Perfringens*

Strains Used: The strains used in this Test Example were those isolated from clinical materials derived from patients infected with the bacteria or reference strains stored in the present Facilities. In this respect, *E. coli* ATCC 25922 and *S. aureus* ATCC 25923 were likewise used as the reference strains for the evaluation of the degree of anti-microbial activity (or for managing the precision of the evaluation). The test solution used in this Test Example was the same as that used in Test Example 7.

Anti-microbial Activity Test: The minimum inhibitory concentration (%) of each sample was determined according to the agar plate dilution method used in the determination of the anti-microbial power of anti-microbial drugs. More specifically, a series of variable GAM agar culture mediums were prepared such that the final concentrations thereof fell within the range of from 8% to 0.125%. The pH value of the culture medium was adjusted to 7.0. The colony of the test stain obtained by cultivating it on the variable GAM agar culture medium over 24 hours was scraped out with a sterilized cotton swab and suspended in Anaerobe broth (available from Difco) to thus form a bacteria-containing solution having a turbidity of Mc Farland No. 1. Then a series of *Sasa* extract-containing plates were inoculated with the resulting suspension (10 μl; inoculum size: $10^6$ cfu) according to the streak-smearing method. Regarding the control strains of *E. coli* and *S. aureus*, each of the colonies formed on a TSA agar culture mediums (available from Difco) was suspended in Anaerobe broth, the turbidity thereof was adjusted to Mc Farland No. 0.5 and then a series of *Sasa* extract-containing plates were inoculated with the resulting suspension (10 μl; inoculum size: $10^5$ cfu) according to the streak-smearing method. In this connection, these samples were cultivated at 35° C. for 18 hours in an anaerobic work station (available from GUNZE Industries, Inc.) and then the culture mediums were visually examined on whether each strain underwent growth or not. The case in which the strain underwent growth was judged to be positive (+). The results thus obtained are listed in the following Table 14.

TABLE 14

Anti-microbial Action of Sasa Extract against a Group of Strains of Gas Gangrene-Causative Bacteria *Clostridium* spp.

| % | *C. bi-fermentans* | *C. sordellii* | *C. novyi* Type A | *C. sporogenes* | *C. septicum* | Sum |
|---|---|---|---|---|---|---|
| 8 | | | | | | |
| 7 | 1 | 2 | | | | 3 |
| 6 | | 1 | | | | 1 |
| 5 | 2 | | | | 1 | 3 |
| 4 | | | | | 4 | 4 |
| 3 | | | | 2 | 6 | 8 |
| 2 | | | | 1 | | 1 |
| 1 | | | 3 | 4 | 1 | 8 |
| 0.5 | | | 1 | | | 1 |
| 0.25 | | | | | | |
| 0.125 | | | | | | |
| Sum | 3 | 3 | 4 | 7 | 12 | 29 |

Consideration

The data listed in Table 14 prove that the *Sasa* extract can inhibit the growth of *C. novyi* and *C. sporogenes* at a concentration of 3%; the growth of *C. septicum* at a concentration ranging from 3 to 5%; and the growth of *C. bifermentans* and *C. sordellii* at a concentration ranging from 5 to 7%. In other words, the anti-microbial activity of the *Sasa* extract against the gas gangrene-related bacteria: *Clostridium* spp. may vary depending on the kinds of bacteria, but it is proved that the *Sasa* extract could inhibit the growth of the whole strains examined herein if the extract is present in a concentration of 7%. When the *Sasa* extract is applied to the wound part for the purpose of preventing the occurrence of any gas gangrene, it is desirable to control the pH value of the extract to 7 and to adjust the concentration thereof to 7%.

TEST EXAMPLE 9

Anti-microbial Activities of *Sasa* Extract against 16 Strains of *Propionibacterium Acnes*

Strains Used Herein: There were used 16 strains in all comprising *P. acnes* ATCC 11827 and 15 strains of *P. acnes* clinically isolated (GAI-10341, GAI-10342, GAI-10343, GAI-10344, GAI-10345, GAI-10346, GAI-10347, GAI-10348, GAI-10349, GAI-10350, GAI-10351, GAI-10352, GAI-10353, GAI-10354, GAI-10355). These clinically isolated strains are isolated from dermatological patients infected with these bacteria and stored in the present Facilities. The test solution used in this Test Example was the same as that used in Test Example 7. Sterilized distilled water was used for the dilution.

Anti-microbial Activity Test: The minimum inhibitory concentration (%) of each sample was determined according to the agar plate dilution method used in the determination of the anti-microbial power of anti-microbial drugs. More specifically, the measurement was carried out according to the standard technique specified in the Chemotherapy Society of Japan. A series of variant GAM agar plates (available from NISSUI Pharmaceutical Co., Ltd.) each containing the *Sasa* extract were prepared in such a manner that the final concentrations of the extract were equal to 12.5, 6.25, 3.13, 1.56 and 0.78%, respectively, The *Sasa* extract aqueous solution and the GAM agar culture medium (two-fold) were admixed together at a mixing ratio of 1:1 to thus prepare a *Sasa* extract-containing agar culture medium having a desired *Sasa* extract concentration. In this connection, the pH value of the culture medium was not adjusted.

A series of *Sasa* extract-containing plates were inoculated with one platinum loop of the high density growth site of each test strain obtained by cultivating the same for 48 hours on a *Brucella* HK semifluid culture medium (available from KYOKUTO Pharmaceutical Co., Ltd.) according to the streak smearing method. One platinum loop of the culture medium included bacterial cells at a density of $10^8$ cells/ml under the experimental conditions of this Test Example. In this connection, these samples were cultivated at 35° C. for two days in an anaerobic work station (available from GUNZE Industries, Inc.) and then the culture mediums were visually examined on whether each strain underwent growth or not. The case in which the strain underwent growth was judged to be positive (+).

Results:

The minimum inhibitory concentration (MIC) of the *Sasa* extract required for completely inhibiting the 16 strains of *P. acnes* was found to be 6.25% (see the following Table 15). The *Sasa* extract showed the significant inhibition of 12 strains out of the 16 strains of *P. acnes* at a concentration of 3.13% as compared with the control culture medium free of any *Sasa* extract, but the *Sasa* extract concentration of 6.25% was required for the complete inhibition of these 16 strains.

TABLE 14

Anti-microbial Activities of Sasa Extract against 16 Strains Belonging to the Genus *Propionibacterium acnes*

| Minimum Inhibitory Concentration of Sasa Extract (%) | Number of Strains |
|---|---|
| 12.5 | 0 |
| 6.25 | 16 |
| 3.13 | 0 |
| 1.56 | 0 |
| 0.78 | 0 |
| Total | 16 |

Consideration

The concentration of the *Sasa* extract required for the inhibition of *S. aureus* involved in the *acne vulgaris* was found to be 3.13%, but the concentration of the *Sasa* extract required for the complete inhibition of the whole strains of *P. acnes* was found to be not less than 3.13% and not more than 6.25%, as a result of the investigation of this Test Example. Since *P. acnes* serves as an important exacerbation factor of the *acne vulgaris* along with *S. aureus*, it would be considered to be suitable to use the concentration of the *Sasa* extract in the order of 6.25% which permits the complete inhibition of the growth of *P. acnes*, when it is intended to treat *acne vulgaris* using the *Sasa* extract.

The precise mechanism of such anti-microbial action of the *Sasa* extract has not yet been dearly elucidated, but the *Sasa* extract derived from plants may have a working mechanism different from those observed for a variety of conventional anti-microbial drugs derived from *Actinomycetes* and fungi and the mechanism is quite interesting from the viewpoint of the development of the drug-resistance.

TEST EXAMPLE 10

Anti-microbial Activities of *Sasa* Extract against 26 Strains of *Propionibacterium acnes* Derived from Acne Strains Used: There were used clinically isolated 26 strains of *P. acnes* in all. These clinically isolated strains are isolated from patients suffering from acne and stored in the present Facilities. The test solution used in this Test Example is the same as that used in Test Example 7 and the solution is one having a concentration of 50% and an acidic pH value (about 5.0). Sterilized distilled water was used for the dilution.

Anti-microbial Activity Test: The minimum inhibitory concentration of each sample was determined according to the agar plate dilution method used in the determination of the anti-microbial power of anti-microbial drugs. More specifically, the measurement was carried out according to the standard technique specified in the Chemotherapy Society of Japan. A series of variant GAM agar plates (available from NISSUI Pharmaceutical Co., Ltd.) each containing the *Sasa* extract were prepared in such a manner that the final concentrations of the extract were equal to 8, 7, 6, 5, 4, 3, 2, 1 and 0.5%, respectively. The pH values of these agar plates were adjusted to about 7.0. The colony obtained by cultivating each test strain for 48 hours on a GAM agar culture medium was suspended in Anaerobe Broth to thus prepare a bacterial cell solution containing a desired number of bacterial cells. In this connection, these samples were cultivated at 35° C. for two days in an anaerobic work station (available from GUNZE Industries, Inc.) and then the culture mediums were visually examined on whether each strain underwent growth or not.

Results and Consideration:

The distribution of the sensitivity to a variety of anti-microbial drugs was used as reference data, although they were not obtained through the tests simultaneously carried out. In this Test Example, it was difficult to judge the end point unlike the previous experiments carried out without controlling the pH value of the culture medium.

TABLE 16

Sensitivity of *P. acnes* (26 Strains) to Sasa Extract and Various Kinds of Anti-microbial Drugs

| Drug | MIC50(μg/ml) | MIC80(μg/ml) | MICRange(μg/ml) |
|---|---|---|---|
| Nadifloxacin | 0.19 | 0.19 | 0.39~0.10 |
| Ofloxacin | 0.39 | 0.39 | 0.78~0.39 |
| Minocycline | 0.05 | 0.10 | 0.39~0.05 |
| Tetracycline | 0.19 | 0.19 | 1.56~0.19 |
| Clindamycin | 0.10 | 0.19 | 0.78~0.025 |
| Extract | MIC50(%) | MIC80(%) | MIC Range(%) |
| Sasa Extract | 6% | 6% | 8~3% |

TEST EXAMPLE 11

Anti-microbial Activity of *Sasa* Extract against *Lactobacllus* spp.

Strains Used: There were used reference strains stored in the present Facilities and shown in the following Table 17. These strains were purchased from ATCC and JCM and they are stored in the present Facilities. In this connection, the controls used herein were *Prevotella bivia* ATCC 29303, *Porphyromonas asaccharolytica* ATCC 25260 and *Bacteroides fragilis* N-1 and N-2, which were selected from the typical microorganisms relatively frequently isolated from the vaginae of women suffering from bacterial vaginosis and the infectious diseases observed in the gynecological field. Moreover, *Escherichia coli* ATCC 25922 and *Staphylococcus aureus* ATCC 25923 were likewise used for the same purpose and as the reference strains for the sensitivity-determination (or for managing the precision of the determination). The test solution used in this Test Example was the same as that used in Test Example 7.

In this respect, when the stock solution of the *Sasa* extract was diluted with sterilized distilled water and the diluted solution was then allowed to stand for a while, liver-colored precipitates were sometimes formed therein, but the diluted solution was admixed with the culture medium after sufficiently stirring the solution to thus uniformly disperse the precipitates.

Anti-microbial Activity Test: The minimum inhibitory concentration (MIC) of each sample was determined according to the agar plate dilution method used in the determination of the anti-microbial power of anti-microbial drugs. More specifically, the measurement was carried out according to the standard technique specified in the Chemotherapy Society of Japan. A series of variant GAM agar plates (available from NISSUI Pharmaceutical Co., Ltd.) each containing the *Sasa* extract were prepared in such a manner that the final concentrations of the extract were equal to 10, 9, 8, 7, 6, 5, 4, 3, 2, 1 and 0.5%, respectively. The plates having high *Sasa* extract concentrations ranging from 10 to 6% were prepared by mixing the *Sasa* extract and the two-fold diluted agar culture medium at a 1:1 mixing ratio (final pH values thereof falling within the range of from 5.3 to 5.5); and the plates having low *Sasa* extract concentrations ranging from 5 to 0.5% were prepared by mixing the *Sasa* extract having a concentration ranging from 50% to 5% and the one-fold diluted agar culture medium at a 1:9 mixing ratio (final pH values thereof falling within the range of from 5.5 to 6.0) to thus prepare the desired *Sasa* extract-containing agar culture mediums.

In addition, the investigation of the anti-microbial power was carried out under weaker acidic to neutral environments in addition to the investigation under acidic conditions (pH 5.3 to 6.0). Culture mediums, each having a pH value ranging from 6.5 to 7.0, were prepared by controlling the pH thereof with a 2N NaOH aqueous solution after the addition of the *Sasa* extract.

Preparation of Bacteria-Containing Solution for Inoculation: The colony of the test strain obtained by cultivating it on *Brucella* NK blood-containing agar culture medium over 48 hours was scraped out with a sterilized cotton swab and suspended in Anaerobe broth MIC (available from Difco) to thus form a bacteria-containing solution having a turbidity of Mc Farland No. 1. Then a series of *Sasa* extract-containing plates were inoculated with the resulting suspension (10 μl; inoculum size: $10^6$ cfu) according to the streak-smearing method. Regarding the control strains, each of the colonies formed on a TSA agar culture mediums was suspended in Anaerobe broth MIC, the turbidity thereof was adjusted to Mc Farland #1 and then a series of *Sasa* extract-containing plates were inoculated with the resulting suspension (10 μl; inoculum size: $10^6$ cfu) according to the streak-smearing method. In this Test Example, regarding *E. coli* ATCC 25922 and *S. aureus* ATCC 25923, MIC values were likewise determined for the bacterial solutions having Mc Farland #½ and those obtained by diluting, 10 times and 100 times, the bacterial solution having a turbidity of Mc Farland #½ to thus investigate the effect of the inoculum size on the MIC value.

In this connection, these samples were cultivated at 35° C. for 18 hours in an anaerobic work station (available from GUNZE Industries, Inc.) and then the culture mediums were visually examined on whether each strain underwent growth or not. The case in which the strain underwent growth was judged to be positive (+).

Results:

Table 17 shows the minimum inhibitory concentrations of the *Sasa* extract as determined under the acidic experimental conditions (pH ranging from 5.3 to 6.0) without controlling the pH value. More specifically, the MIC values were found to be 7 to 8% for 4 strains of the following 4 kinds of bacteria: *Lactobacllus casei* ss. *casei, Lactobacllus. brevis* ss. *brevis, Lactobacllus acidophilus* and *Lactobacllus salivarius*; and not less than 10% for 5 strains of 5 kinds of bacteria other than these 4 strains of the 4 kinds of bacteria. Moreover, the minimum inhibitory concentrations thereof were likewise simultaneously determined for *P. bivia* ATCC 29303, *P. asaccharolytica* ATCC 25260 and they were both found to be 0.5%, while the minimum inhibitory concentrations of the *Sasa* extract for the foregoing two precision-managing strains: *E. coli* ATCC 25922 and *S. aureus* ATCC 25923 were found to be 4%, as determined by the foregoing method.

Table 17 also shows the minimum inhibitory concentrations of the *Sasa* extract as determined under the experimental conditions in which the pH values were adjusted (to the range of from 6.8 to 7.1). More specifically, the minimum inhibitory concentrations thereof were found to be 7% for the following two strains of two kinds of bacteria: *L. brevis* ss. *brevis, L. acidophilus*; and ≧9% for 7 strains of 7 kinds of bacteria other than the foregoing two strains of two kinds of bacteria. Moreover, the MIC values were found to be 1% for *P. bivia*; and 0.5% for *P. asaccharolytica*. Further, the MIC values were found to be 6% for *E. coli* ATCC 25922 and *S. aureus* ATCC 25923.

In this connection, the effect of the inoculum size on the MIC value observed when determining MC values under the pH-adjusted experimental conditions (pH ranging from 6.4 to 7.0) was investigated using *E. coli* ATCC 25922 and *S. aureus* ATCC 25923. As a result, the MIC values for *S. aureus* were read to be 6% when using one platinum loop each of the bacterial solutions whose turbidity ranged from Mc Farland #1 to ½ (>$10^8$/ml); and 3% when using one platinum loop each of the bacterial solutions obtained by diluting, 10 times ($10^7$/ml) and 100 times ($10^6$/ml), the bacterial solution having a turbidity of Mc Farland #½. Regarding *E. coli*, the degree of growth thereof observed within the sub-MIC region was stepwise lowered due to the variation of the inoculum size, but there was not observed any variation in the read MIC values and the MIC value thereof for this bacterium was found to be 6% in the both cases.

Consideration:

It has been demonstrated that the growth of several pathogenic bacteria can be inhibited by the use of the *Sasa* extract having a concentration ranging from 6.25% to 3.13% or lower. The inventors have recognized that it is quite important to collect information concerning the anti-microbial activities of the *Sasa* extract against non-pathogenic (sprophytic) bacteria in addition to the anti-microbial activities against these pathogenic bacteria and the inventors have thus conducted this Test Example.

It has been proved that most of the bacteria belonging to the genus *Lactobacllus* spp. play quite important roles on the human mucous membranes from the viewpoint of biological protection. The inventors of this invention have isolated 91 strains of *Lactobacllus* spp. from vaginae of 29 healthy women in pregnancy and identified them in detail. As a result, it was found that the *Lactobacllus crispatus* showed the highest isolation frequency of 48 strains (52.7%), that *Lactobacllus gasseri* was subsequent thereto (19 strains; 20.85%) and that other bacteria thus isolated were, for instance, *Lactobacllus vaginalis, Lactobacllus fermentum, Lactobacllus plantarum, L. salivarius*. Among them, 100% of the *Lactobacllus crispatus* produces hydrogen peroxide and it is a typical of *Lactobacllus* spp. having a high hydrogen peroxide-producing ability and it plays a particularly important role in the mechanism of protecting the vaginae and uterine mucosa of women from any infection, along with two kinds of bacteria: *L. gasseri* and *L. vaginalis*. Regarding the latter two bacteria, there has been reported that they include strains capable of producing hydrogen peronide although 100% thereof cannot always produce the same. In this investigation, it has been clear that the anti-microbial activities of the *Sasa* extract against *L. crispatus* and *L. gasseri* as the hydrogen peroxide-producing bacteria belonging to the genus *Lactobacllus* spp. is found to be not less than 10% as expressed in terms of MIC or that the antimicrobial activities are quite weaker than those against the typical pathogenic facultative bacteria, having an MIC value of 4%, such as *E. coli, S. aureus* and those against the typical purulent anaerobic bacteria, having an MIC values ranging from 0.5 to 4%, such as *P. bivia, P. asaccharolytica* and *B. fragilis*.

Moreover, the *Sasa* extract shows a pH value very close to that of the vaginal environment and it has been known that the *Sasa* extract shows a higher anti-microbial activity under neutral conditions rather than the alkaline conditions and shows a higher anti-microbial activity under the acidic conditions rather than the neutral conditions. The MIC value of the *Lactobacllus* spp. does not undergo any significant change even under the weakly acidic experimental conditions, which can be established by slightly shifting the pH value of the environment towards the neutral region wherein the anti-microbial activities of the extract against the reference bacteria: *E. coli* and *S. aureus* are reduced in the order of about two-fold dilutions.

Further the inventors of this invention have also found that bacteria belonging to, for instance, the genus *L. gasseri, L. fermentum, L. paracasei, L. plantarum, L. salivarius* and *L. crispatus* are isolated from the intestinal tracts of the women in pregnancy and neonates in a relatively high rate. Among these bacteria of *Lactobacllus* spp., the *Sasa* extract shows rather higher MIC values on the order of not less than 7% against the bacteria of *Lactobacllus* spp. other than *L. crispatus* and *L. gasseri*, which are isolated from the vaginae in a high isolation rate.

The foregoing would suggest that the anti-microbial activity of the *Sasa* extract is, by nature, low for *Lactobacllus* spp. as bacteria useful in the vagina and the digestive tracts as compared with the activities observed for bacteria which are estimated as having higher pathogenicity. Simultaneously, this also suggests that the foregoing may be quite excellent characteristics of the *Sasa* extract when using this substance in the gynecology, for instance, vaginae and digestive tracts.

TABLE 17

Anti-microbial Activities of Sasa Extract Against Bacteria Belonging to *Lactobacillus* spp. Group

| Name of Bacterium | Minimum Inhibitory Concn. Of Sasa Extract (%) | |
|---|---|---|
| | pH-uncontrolled | pH-controlled |
| *Lactobacillus* | | |
| *L. crispatus* GAI97504 | >10 | >=9 |
| *L. gasseri* GAI97505 | >10 | >=9 |
| *L. casei* ss. *casei* JCM1134 | 7 | >=9 |
| *L. brevis* ss *brevis* JCM1059 | 7 | 7 |
| *L. acidophilus* JCM1132 | 7 | 7 |
| *L. salivarius* ss. *salivarius* JCM1231 | 8 | >=9 |
| *L. reuteri* JCM1112 | >10 | >=9 |
| *L. plantarum* JCM1149 | >10 | >=9 |
| *L. fermentum* JCM1173 | >10 | >=9 |
| *Prevotella* | | |
| *P. bivia* ATCC25903 | <=0.5 | 1 |
| *Poprphyromonas* | | |
| *P. asaccharolytica* ATCC25260 | <=0.5 | <=0.5 |
| *Bacteroides* | | |
| *B. fragilis* N | 4 | NT |
| *B. fragilis* N-10 | NT | 5 |
| *Escherichia coli* ATCC25922 | 4 | 6 |
| *Staphylococcus aureus* ATCC25923 | 4 | 6 |

*: Inoculum size: One platinum loop of Mc Farland#1

TEST EXAMPLE 12

Anti-microbial Activities against *Escherichia coli* Methicillin Resistant *Staphylococcus aureus* and *Pseudomonas aeruginosa*

The inventors of this invention have found that the *Sasa* extract shows anti-microbial activities against bacteria of the genus *Escherichia coli* which are quite important as causative bacteria of a variety of purulent infectious diseases; Methicillin resistant *Staphylococcus aureus* (MRSA) showing multiple drug resistance against a variety of anti-microbial drugs; and *Pseudomonas aeruginosa* showing a strong tendency of withstanding a large number of anti-microbial drugs like MRSA The inventors of this invention have determined the anti-microbial activities of the *Sasa* extract against the anaerobic bacteria according to the agar plate-dilution method using a variant GAM agar culture medium as the sensitivity-determining culture medium, which is recommended as a means for determining anti microbial activities against anaerobic bacteria.

In this Test Example, however, the inventors investigated the anti-microbial activities against facultative bacteria and aerobic bacteria according to the agar plate-dilution method which made use of Mueller Hinton Agar as the activity-determining culture medium, the method being recommended as a means for determining anti-microbial activities against facultative bacteria, using not less than 10 strains each of the facultative and aerobic bacteria belonging to the genus *E. coli, S. aureus* and *P. aeruginosa*, isolated from patients.

Materials and Methods:

Strains Used: There were used, in this Example, 14 strains of *E. coli,* 14 strains of Methicillin resistant *S. aureus* and 13 strains of *P. aeruginosa.* In addition, *Escherichia coli* ATCC 25922 and *Staphylococcus aureus* ATCC 25923 were likewise used for the same purpose and as the reference strains for the sensitivity-determination (or for managing the precision of the determination). The test solution used in this Test Example was the same as that used in Test Example 7. Sterilized distilled water was used for the dilution of the test solution.

Anti-microbial Activity Test: The minimum inhibitory concentration (MIC) of each sample was determined according to the agar plate dilution method used in the determination of the anti-microbial power of anti-microbial drugs against facultative bacteria. More specifically, the measurement was carried out according to the standard technique specified in the Chemotherapy Society of Japan, as much as possible. A series of Mueller Hinton agar plates (available from Difco) each containing the *Sasa* extract were prepared in such a manner that the final concentrations of the extract were equal to 7, 6, 5, 4, 3, 2, 1, 0.5, 0.25, 0.125, 0.063 and 0.032%, respectively. The plates having high *Sasa* extract concentrations ranging from 7 to 6% were prepared by mixing the *Sasa* extract having a concentration ranging from 14 to 12% and the Mueller Hinton agar culture medium having a two-fold concentration at a 1:1 mixing ratio; and the plates having low *Sasa* extract concentrations ranging from 5 to 0.032% were prepared by mixing the *Sasa* extract having a concentration ranging from 50% to 0.32% and the Mueller Hinton agar culture medium having a one-fold concentration at a 1:9 mixing ratio to thus prepare the desired *Sasa* extract-containing agar culture mediums. The pH values of these culture mediums were adjusted to the range of from 6.5 to 7.3 using a 2N NaOH aqueous solution.

In addition, a series of *Sasa* extract-containing agar culture mediums were prepared using a variant GAM agar culture medium (available from NISSUI Pharmaceutical Co., Ltd.) instead of the Mueller Hinton agar culture medium, followed by inoculation thereof with *E. coli* and MRSA using the same bacteria-containing solution for inoculation and the cultivation thereof overnight under anaerobic conditions to thus determine the MIC values of these samples. In this case, the pH values of these culture mediums were adjusted to the range of from 6.7 to 7.3 using a 2N NaOH aqueous solution.

Preparation of Bacteria-Containing Solution for Inoculation and Judgment:

The colony of the test strain obtained by cultivating it on TSA agar culture medium over 24 to 48 hours was scraped out with a sterilized cotton swab and suspended in Mueller Hinton broth (available from Difco) to thus form a bacteria-containing solution having a turbidity of Mc Farland No. 1. The resulting bacteria-containing solution (10 µl) was suspended in 1 ml of Mueller Hinton broth and 5 µl of the resulting suspension was inoculated in the series of the *Sasa* extract-containing plates according to the streak-smearing method.

After cultivating these culture medium inoculated at 35° C. for 20 hours in an aerobic environment and the culture mediums were visually examined on whether each strain underwent growth or not. Regarding the plates anaerobically cultivated, the growth of the strain was judged after the cultivation thereof overnight, followed by allowing it to stand overnight under the atmospheric conditions and the culture medium was further examined on whether the strain again underwent growth or not.

Results:

The minimum inhibitory concentrations (MIC) of the *Sasa* extract against the bacteria of the genus *E. coli* as determined under the pH-controlled experimental conditions were found to be distributed within the range of from 2 to 3% and the MIC50% value was found to be 2%. On the other hand, the MIC values of the extract against MRSA were found to be distributed within the range of from 0.25 to 0.5% and the MIC50% value was found to be 0.5%. In addition, the MIC values of the extract against *P. aeruginosa* were found to be 1% for all of the strains examined.

Moreover, the MIC value thereof for the precision-managing strain or *E. coli* ATCC 25922 was found to be 2% under the such experimental conditions as the neutral environment and the aerobic cultivation conditions in the Mueller Hinton culture medium and the MIC value for *S. aureus* ATCC 25923 was found to be 0.5%.

The MIC 50% value of the *Sasa* extract was found to be 8% for the clinically isolated 14 strains of *E. coli* as determined under the anaerobic environment using the variant GAM agar culture medium, while that for the clinically isolated 14 strains of *S. aureus* was found to be 3%. Further, the MIC values of the *Sasa* extract against the precision-managing strains were found to be 8% for *E. coli* ATCC 25922 and 3% for *S. aureus* ATCC 25923 as determined under the neutral environment and the anaerobic cultivation conditions in the variant GAM agar culture medium.

Consideration:

The data concerning the MIC values of the *Sasa* extract as determined in this Test Example according to the standard technique specified in the Chemotherapy Society of Japan, as much as possible indicate that the *Sasa* extract has an MIC value of not more than 1% for the both MRSA and *P. aeruginosa* under an approximately neutral environment and that it has thus a very strong anti-microbial activities against these bacteria.

It has been well known that the MIC values of a certain drug against bacteria may vary depending on various experimental conditions including, for instance, the components and pH values of culture mediums used, the presence of additives such as blood, the inoculum size and the cultivation environment used. The inventors of this invention have investigated the MIC values of the *Sasa* extract using, as subjects, anaerobic bacteria, which require the use of dietetically complicated components and grow only in an anaerobic environment free of any free oxygen atoms, such as *Clostridium tetani, Clostridium perfringens, Propionibacterium acnes* and *Bacteroides fragilis.* In the determination of these values, the inventors used *E. coli* ATCC 25922 and *S. aureus* ATCC 25923 as measurement precision-managing strains, but there have not yet been simultaneously determined the MC values of the *Sasa* extract against these precision-managing strains under the anaerobic environment and the MC values thereof against these bacteria in the measuring environment originally used for the facultative bacteria and compared these MIC values with one another. The inventors have investigated this point and made the difference between these MIC values clear. It was observed that when using a variant GAM agar culture medium as the sensitivity-determining culture medium under an anaerobic environment, the MIC value of the *Sasa* extract thus determined was found to be not less than 7% for *E. coli* ATCC 25922 and that the MIC value was greatly shifted towards the resistant-side from the value of 2% observed when the strain was cultivated in a Mueller Hinton culture medium under an aerobic environment. In addition, the MIC value of the Sasa extract thus determined was found to be 3% for S. aureus ATCC 25923 and the MIC value was greatly shifted towards the resistant-side as compared with the value of 0.5% observed when the strain was cultivated in a Mueller Hinton culture medium under an aerobic environment. The MIC 90% values of the Sasa extract against the 14 strains of MRSA was found to be 3% as determined in the measuring environment similar to that used for the anaerobic bacteria. The growth of S. aureus is inhibited when cultivated under the anaerobic conditions to thus form colonies like Mueller Hinton agar were investigated and compared with one another, it was confirmed that the behavior of the MIC values varied depending on the kinds of bacteria. For instance, the MIC value for E. coli ATCC 25922 as determined under the anaerobic cultivation conditions using Mueller Hinton agar was identical to that observed under the aerobic cultivation conditions, while the MIC value for S. aureus ATCC 25923 as determined under the anaerobic cultivation conditions was 4 times greater than that obtained under the anaerobic cultivation conditions although the experimental conditions were the same as those used in case of E. coli ATCC 25922. It would be considered that a variety of factors may complicatedly be involved in this phenomenon.

TABLE 18

Distribution of MIC of Sasa Extract Against *Escherichia coli*, *Pseudomonas aeruginosa* and *Staphylococcus aureus*

| MIC (%) | E. coli Aerobic* | E. coli Anaerobic* | P. aeruginosa Aerobic | P. aeruginosa Anaerobic | S. aureus (MRSA) Aerobic | S. aureus (MRSA) Anaerobic |
|---|---|---|---|---|---|---|
| 8 | | 14* | | | | (14) |
| 7 | | | | | | |
| 6 | | | | | | |
| 5 | | | | | | |
| 4 | | | | | | 5* |
| 3 | 10 | | | | | 7 |
| 2 | 4* | | | | | 2 |
| 1 | | | 13* | | | |
| 0.5 | | | | | 8* | |
| 0.25 | | | | | 6 | |
| 0.125 | | | | | | |
| Total | 14 | | 13 | | 14 | 14 |
| MIC range | 3~2% | 8% | 1% | ND | 0.5~0.25% | 4~2% |
| MIC 50% | 2% | 8% | 1% | ND | 0.5% | 3% |

*Aerobic: Mueller Hinton agar, Aerobic cultivation;
Anaerobic: Variant GAM agar culture medium, anaerobic cultivation.

dewdrops and therefore, this sometimes made it difficult to clearly judge or determine the end point. The plates once evaluated were additionally allowed to stand overnight in an aerobic environment to thus confirm whether the dewdrop-like colonies again underwent growth or not and there were observed three cases in which points on colonies judged to be positive in growth never underwent any growth after the cultivation thereof overnight. Accordingly, when the anti-microbial activity of the Sasa extract was determined in an anaerobic environment and S. aureus ATCC 25923 used as a precision-managing strain formed dewdrop-like colonies in the cultivation environment, the method for the determination of the MIC value should be reconsidered and it would, for instance, be necessary to confirm the presence of any ability of again undergoing growth. From the foregoing, it has been proved that the MIC values for the facultative bacteria as determined under the same conditions used for the determination of the values for the anaerobic bacteria are shifted towards the resistant-side and they are 6 to 8 times greater than that observed in the aerobic environment. It is quite interesting to know whether the reason for this is due to the difference in components between Mueller Hinton agar and variant GAM agar culture mediums or due to the difference between the anaerobic cultivation and the aerobic cultivation, which is observed for aminoglycosides as anti-microbial drugs. In this connection, when the MIC values as determined under the anaerobic and aerobic cultivation conditions using The anaerobic cultivation of P. aeruginosa was not carried out.

Reference:

TABLE 19

Comparison of MIC values of Sasa extract against 3 reference strains: *Escherichia coli*, *Pseudomonas aeruginosa*, *Staphylococcus aureus* as determined according to the standard method specified by the Chemotherapy Society of Japan using Mueller Hinton Agar as sensitivity-measuring culture medium:

| Organism ATCC No | Inoculum Size | MIC (%) Aerobic pH 7.0 pH 5.0 | | MIC (%) Anaerobic pH 7.0 |
|---|---|---|---|---|
| *Escherichia coli* ATCC 25822 | high | NT | | 2 |
| | low | 2* | | 2 |
| *Pseudomonas aeruginosa* ATCC | high | NT | | (1) |
| | low | NT | | (1) |
| *Staphylococcus aureus* ATCC 25923 | high | NT | | 2 |
| | low | 0.5** | | 2 |

High: 10 μl of the bacterial solution having a turbidity of Mc Farland No. 1;
Low: 10 μl of a bacterial solution obtained by diluting the bacterial solution having a turbidity of Mc Farland No. 1 100 times.
(1): The MIC value was undetectable in the anaerobic cultivation, but it was found to be 1% when estimating the same after continuing the aerobic cultivation of the strain.
NT: Not tested.

TABLE 20

Effect of pH Value of Culture Medium on MIC Values

| Name of Bacterium | | pH 5.0 | pH 7.0 |
|---|---|---|---|
| E. coli | high | <=5 | 8 |
|  | low | <=5 | 8 |
| S. aureus | high | <=5 | 8 |
|  | low | <=5 | 5 |
| P. aeruginosa | high | <=5 | <=5 |
|  | low | <=5 | <=5 |

TABLE 21

Variant GAM Agar Culture Medium, Anaerobic Cultivation, Cultivation Over 24 Hours

| | Sasa extract E. coli | | Sasa extract S. aureus | | Nippon HARUMA S. aureus | | Nippon HARUMA E. coli | |
|---|---|---|---|---|---|---|---|---|
| | Low | High | Low | High | Low | High | Low | High |
| 4    | −  | −  | −  | −  |    | −  | +  | +  |
| 3    | −  | +  | −  | −  |    | −  | +  | +  |
| 2    | +w | +  | −  | −  |    | −  | +  | +  |
| 1    | +  | +  | −  | −  | +  | +  | +  | +  |
| 0.5  | +  | +  | −  | +  | +  | +  | +  | +  |
| 0.25 | +  | +  | +  | +  | +  | +  | +  | +  |
| 0    |    | +  |    | +  |    | +  |    | +  |
|      | 3  | 4  | 0.5| 1  | ND | 2  | >4 | >4 |

Variant GAM Agar Culture Medium, Anaerobic Cultivation, Cultivation Over 24 Hours.

TEST EXAMPLE 13

Anti-microbial Action of *Sasa* Extract against Bacterial Vaginosis-Related (BV-Related) Microorganisms 1. As for the Strains: *Prevotella bivia* and Pigmented *Prevotella* spp.

The anti-microbial activities of the *Sasa* extract were first investigated for *Prevotella bivia* and Pigmented *Prevotella* spp., among the bacteria classified into the BV-related bacteria.

Strains Used: There were used, in this Test Example, strains of *Prevotella bivia* (14 strains in all) and 9 strains of Pigmented *Prevotella* spp. (*Prevotella intermedia, Prevotella melaninogenica*). The *Prevotella bivia* was isolated from a woman's vagina in the first half of 1990 and Pigmented *Prevotella* spp. was isolated from a variety of clinical materials in 2002 and these strains are stored in the present Facilities. In addition, *Escherichia coli* ATCC 25922 and *Staphylococcus aureus* ATCC 25923 were likewise used as the measurement precision-managing strains. The test solution used in this Example was identical to that used in Test Example 7, which was an acidic (pH: about 5.0) solution having a concentration of 50% (w/v). Sterilized distilled water was used for the dilution thereof.

Anti-microbial Activity Test: The minimum inhibitory concentration of the *Sasa* extract was determined according to the agar plate-dilution method used in the determination of the anti-microbial power of anti-microbial drugs. A series of variant GAM agar plates (available from NISSUI Pharmaceutical Co., Ltd.) in such a manner that they contained the *Sasa* extract in the final concentrations of 4, 3, 2, 1, 0.5, 0.25 and 0.125%, respectively. The *Sasa* extract was mixed with the agar culture medium at a mixing ratio of 1:9 to thus form an agar culture medium containing the *Sasa* extract at a desired concentration. In this connection, a 2N NaOH aqueous solution was used for the control of the pH value (7.0 to 7.3) of the culture medium.

The colony obtained by cultivating the test strain in *Brucella* HK blood-containing culture medium (available from KYOKUTO Pharmaceutical Co., Ltd.) for 48 hours was suspended into Anaerobe Broth MIC (available from Difco) to thus form a bacterial solution having a turbidity of Mc Farland #1, the resulting bacterial solution was diluted 10 times and one platinum loop (10 μl) of the diluted bacterial solution was inoculated into a series of *Sasa* extract-containing plates according to the streak-smearing method. One platinum loop of the diluted bacterial solution comprises about $10^4$ bacterial cells therein under the present experimental conditions. These samples were cultivated at 35° C. for two days in an anaerobic work station (available from GUNZE Industries, Inc.) and then the culture mediums were visually examined on whether each strain underwent growth or not. The case in which the strain underwent growth was judged to be positive (+).

In this connection, the MIC values of the *Sasa* extract against *E. coli* ATCC 25922 and *S. aureus* ATCC 25923 were both found to be >5% as determined under the present experimental conditions.

Results:

It was found that the *Sasa* extract could completely inhibit the growth of *P. bivia* at a concentration of 0.5% and the growth of Pigmented *Prevotella* spp. at a concentration of 1%. Moreover, the MIC50% values of the *Sasa* extract against the 14 strains of *P. bivia* and Pigmented *Prevotella* spp. were both found to be 0.5%.

TABLE 22

Anti-microbial Activities of Sasa extract Against 14 Strains of *Prevotella bivia* and 9 Strains of Pigmented *Prevotella* spp.

| Minimum Inhibitory Concn. of Sasa Extract (%) | *P. bivia* | Pigmented *Prevotella* spp |
|---|---|---|
| 4 | 0 | |
| 3 | 0 | |
| 2 | 0 | |

TABLE 22-continued

Anti-microbial Activities of Sasa extract Against 14 Strains of *Prevotella bivia* and 9 Strains of Pigmented *Prevotella* spp.

| Minimum Inhibitory Concn. of Sasa Extract (%) | *P. bivia* | Pigmented *Prevotella* spp |
|---|---|---|
| 1 | 0 | 2 |
| 0.5 | 14 | 7 |
| 0.25 | 0 | 0 |
| 0.125 | 0 | |
| Sum | 14 | 9 |

Consideration:

The vagina of the healthy woman is a treasure-house of anaerobic and aerobic bacteria. Bacteria of *Lactobacillus* spp. are most predominantly present in the normal bacterial flora of the woman's birth canal and play an important role in the maintenance of the cleanliness in the vagina. However, it has been known that there are likewise present, in the bacterial flora, anaerobic gram-positive *cocci* such as *Peptostreptococcus anaerobius*, and anaerobic gram-negative *bacilli* such as *Prevotella* spp. (such as *Prevotella melaninogenica* and *Prevotella intermedia*) and *Bacteroides* spp., which are also known as opportunistic pathogens although the densities (population) thereof are low, that they may undergo abnormal growth in the conditions called bacterial vaginosis and that they are referred to as bacterial vaginosis-related microorganisms. The bacterial vaginosis is a disease accompanied by the secretion of milk-like fluor (or leukorrhea) giving out a bad smell and this disease has been discussed in relation to a variety of abnormalities observed in the perinatal period such as a high susceptibility to STD, the premature delivery and the premature rupture of membranes and in connection with the progress to pelvic inflammatory diseases (PID).

It has been known that *P. bivia* and Pigmented *Prevotella* spp. are quite important bacterial species related to the severity and intractability of the diseases, among the bacterial vaginosis-related microorganisms.

The foregoing investigation makes it clear that the *Sasa* extract shows very high anti-microbial activities against these bacteria of *P. bivia* and Pigmented *Prevotella* spp.

TABLE 23

List of Causative Pathogen of Infectious Diseases in the field of obstetrics and gynecology

| Disease | Scientific Name | Common Name | Remarks |
|---|---|---|---|
| Gonorrhea Gonorrheal cervical disease | *Neisseria gonorrhoea* | Gonococcus | Bacteria |
| Uterocervical chlamydiosis (cervicitis) | *Chlamydia trachomatis* | *Chlamydia trachomatis* | Bacteria |
| Candidosis Vulvitis Vaginitis | *Candida albicans* | *Candida albicans* | Fungi |
| Vaginal trichomoniasis Vaginitis Urethritis | *Trichomonas vaginalis* | Vaginal *Trichomonas* | Protozoon |
| Bacterial vaginosis(BV) | BV-related microorganism | | Bacteria |
| | *Mycoplasma genitalium* | Genital Mycoplasma | |

TABLE 23-continued

List of Causative Pathogen of Infectious Diseases in the field of obstetrics and gynecology

| Disease | Scientific Name | Common Name | Remarks |
|---|---|---|---|
| | *Gardnerella vaginalis* | Gardnerella | |
| | *Prevotella bivia*\* | *Prevotella bivia* | |
| | Pigmented *Prevotella* spp.\* | Black dyestuff-producing *Prevotella* | |
| | *Porphyromonas* spp.\* | *Porphyromonas* | |
| | *Mobiluncus* spp.\* | *Mobiluncus* | |
| | *Peptostreptococcus* spp.\* | *Peptostreptococcus* | |
| Pudic Herpes | Herpes simplex virus (HSV) | Herpes simplex virus | Virus |
| Syphilis | *Treponema pallidum* | Syphilitic *Treponema* | Bacteria |

\*Anaerobic bacteria.

TEST EXAMPLE 14

Anti-microbial Activities of *Sasa* Extract against Bacterial Vaginosis-Related Microorganisms 2. As to the Strains Belonging to the Genus *Gardnerella vaginalis*

The bacteria of *Gardnerella vaginalis* can be detected in the vaginae of healthy women, but the population thereof is low. *G. vaginalis* is one of bacterium falling under the category of the so-called bacterial vaginosis-related microorganisms which undergo abnormal growth under the conditions called bacterial vaginosis, along with *Mycoplasma homminis*, *Peptostreptococcus anaerobius*, Pigmented *Prevotella* spp., Non-pigmented *Prevotella* spp. and *Porphyromonas* spp. Moreover, the bacteria are very important as causative bacteria of the birth canal infectious diseases. In this Test Example, *G. vaginalis* was investigated.

Materials and Methods:

Strains Used: There were used 11 strains of *G. vaginalis* in all. These strains consist of 2 strains purchased from NCTC and ATCC and clinically isolated 9 strains. The clinically isolated strains are those isolated, by the inventors of this invention, from vaginae of women in the first half of 1990 and stored in the present Facilities. In addition, *Escherichia coli* ATCC 25922 and *Staphylococcus aureus* ATCC 25923 were likewise used as the MIC-measurement precision-managing strains. The test solution used was the same as that used in Test Example 7.

Anti-microbial Activity Test: The minimum inhibitory concentration of the *Sasa* extract was determined according to the agar plate-dilution method used in the determination of the anti-microbial power of anti-microbial drugs. The determination was carried out according to the standard method as specified by the Chemotherapy Society of Japan. A series of *Sasa* extract-containing *Brucella* HK blood-containing agar culture mediums (available from KYOKUTO Pharmaceutical Co., Ltd.) were prepared in such a manner that the final *Sasa* extract concentrations were equal to 8, 7, 6, 5, 4, 3, 2, 1, 0.5, 0.25 and 0.125%, respectively. More specifically, the *Sasa* extract and the *Brucella* HK blood-containing agar culture medium were admixed in a mixing ratio of 1:1 or 1:9 to thus form a *Sasa* extract-containing agar culture medium having a desired *Sasa* extract concentration. In this connection, a 2N NaOH aqueous solution was used for the control of the pH value (pH: 7.0 to 7.3) of the culture medium.

The colony obtained by cultivating the test strain in *Brucella* HK blood-containing culture medium (available from KYOKUTO pharmaceutical Co., Ltd.) for 48 hours was suspended into Anaerobe Broth MIC (available from Difco) to thus form a bacterial solution having a turbidity of Mc Farland #1 and one platinum loop (10 μl) of the resulting bacterial solution was inoculated into a series of *Sasa* extract-containing plates according to the streak-smearing method. In this connection, the inoculum size was set at such a level that the growth in the control culture medium was uniform throughout the smeared area.

These samples were cultivated at 35° C. for two days in an anaerobic work station (available from GUNZE Industries, Inc.) and then the culture mediums were visually examined on whether each strain underwent growth or not. The case in which the strain underwent growth was judged to be positive (+).

Incidentally, the MIC values of the *Sasa* extract against *E. coli* ATCC 25922 and *S. aureus* ATCC 25923 as determined under the experimental conditions used herein were found to be >8% and 8%, respectively.

Results

The MIC of the *Sasa* extract against these 11 strains of *G. vaginalis* were distributed within the range of from 6 to 4% and the MIC50% value thereof was found to be 6%.

TABLE 24

Anti-microbial Activities of Sasa Extract Against 11 Strains of *Gardnerella vaginalis*

| Minimum Inhibitory Concn. of Sasa Extract (%) | Number of Strains |
| --- | --- |
| 8 | 0 |
| 7 | 0 |
| 6 | 7 |
| 5 | 3 |
| 4 | 1 |
| 3 | 0 |
| 2 | 0 |
| 1 | 0 |
| 0.5 | 0 |
| 0.25 | 0 |
| 0.125 | 0 |
| Sum | 11 |

Consideration:

The foregoing investigation makes it clear that the *Sasa* extract permits the complete inhibition of the growth of *G. vaginalis* or a facultative anaerobic bacterium, which is important as one of the bacterial vaginosis-related (BV-related) microorganism, at a concentration of 6%. This clearly indicates that anti-microbial activity of the *Sasa* extract against this bacterium is weaker than those observed for *P. bivia* as a bacterium of Non-pigmented *Prevotella* and *Prevotella melaninogenica* as a bacterium of pigmented *Prevotella*, which belong to the BV-related microorganism. It has been known that the extract never inhibits the growth of a large number of strain of *Lactobacillus* spp. even at a concentration of 8% and therefore, the foregoing results are quite important in the establishment of the concentration of the extract when using the same for living bodies.

Incidentally, it has been proved, in a series of investigation, that the MIC values observed for *E. coli* and *S. aureus* as the reference strains vary depending on the experimental conditions. Although the MIC value is influenced by a variety of factors such as the kind of sensitivity-determining culture medium used, the inoculum size and the conditions for cultivation, the inventors of this invention used *Brucella* HK blood-containing agar culture mediums as the sensitivity-determining culture medium, for the first time. The inventors are under the impression that the MIC values obtained using this culture medium are shifted towards acid side as compared with those obtained using the variant GAM culture medium.

TEST EXAMPLE 15

Anti-Microbial Activities of *Sasa* Extract against Bacterial Vaginosis-Related Microorganism 3. As to *Finegoldia, Micromonas, Peptostreptococcus*

*Finegoldia magna, Micromonas micros, Peptostreptococcus* spp., which are anaerobic bacteria, are bacteria belonging to the bacterial vaginosis-related microorganism, which abnormally proliferate under the conditions of bacterial vaginosis (BV) characterized by the reduction of the intravaginal lactic acid bacteria, the reduction of the intravaginal pH and the milk-like fluor giving out a bad smell (an amine-like smell), like *Prevotella bivia*, Pigmented *Prevotella* spp., *Porphyromonas* spp., *Mycoplasma genitalium* (hommnis) and *Gardnerella vaginalis*. Accordingly, the anti-microbial activities of the *Sasa* extract against anaerobic bacteria, which are bacteria classified into the bacterial vaginosis-related microorganism were investigated in this Test Example.

Materials and Methods:

Strains Used: There were used 21 strains in all consisting of *Peptostreptococcus anaerobius* (5 strains), *Peptostreptococcus asaccharolyticus* (3 strains), *Finegoldia magna* (7 strains) and *Micromonas micros* (6 strains). *Escherichia coli* ATCC 25922 and *Staphylococcus aureus* ATCC 25923 were likewise used as the MIC measurement precision-managing strains. The test solution was the same as that used in Test Example 7.

Anti-microbial Activity Test: The minimum inhibitory concentration of the *Sasa* extract was determined according to the agar plate-dilution method used in the determination of the antimicrobial power of anti-microbial drugs. More specifically, there were prepared a series of variant GAM agar plates (available from NISSUI Pharmaceutical Co., Ltd.) containing the *Sasa* extract at final concentrations of 5, 4, 3, 2, 1, 0.5, 0.25 and 0.125%, respectively. The *Sasa* extract and the agar culture medium were mixed at a mixing ratio of 1:9 to thus form an agar culture medium containing a desired amount of the *Sasa* extract. In this connection, a 2N NaOH aqueous solution was used to adjust the pH value of the culture medium.

The colony obtained by cultivating the test strain in a *Brucella* HK blood-containing agar culture medium (KYOKUTO Pharmaceutical Co., Ltd.) over 48 hours was suspended in Anaerobe Broth MIC (available from Difco) to thus prepare a bacterial solution having a turbidity of Mc Farland #1 and a series of the *Sasa* extract containing plates were inoculated with one platinum loop (10 μl) of the resulting bacterial solution according to the streak-smearing method. One platinum loop of the bacterial solution contains about $10^6$ bacterial cells under the present experimental conditions.

These samples were cultivated at 35° C. for 24 hours in an anaerobic work station (available from GUNZE Industries, Inc.) and then the culture mediums were visually examined on whether each strain underwent growth or not. The case in which the strain underwent growth was judged to be positive (+).

Incidentally, the MIC values of the *Sasa* extract against *E. coli* ATCC 25922 and *S. aureus* ATCC 25923 as determined under the experimental conditions used herein were both found to be ≧5%.

Results:

The *Sasa* extract could completely inhibit these 21 anaerobic coccal strains of *M. micros*, *F. magna*, *P. anaerobius* and *P. asaccharolyticus* at a concentration of 3%. The MIC50% value thereof against anaerobic cocci was found to be 0.5%.

TABLE 25

Anti-microbial Activities of Sasa Extract Against Anaerobic Cocci

| Minimum Inhibitory Concn. (%) | F. magna | M. micros | P. anaerobius | P. asaccharolyticus | Sum |
|---|---|---|---|---|---|
| 5 | 0 | 0 | 0 | 0 | |
| 4 | 0 | 0 | 0 | 0 | |
| 3 | 0 | 0 | 0 | 0 | |
| 2 | 0 | 2 | 0 | 0 | 2 |
| 1 | 2 | 3 | 1 | 0 | 6 |
| 0.5 | 5 | 0 | 4 | 3 | 12 |
| 0.25 | 0 | 1 | 0 | 0 | 1 |
| 0.125 | 0 | 0 | 0 | 0 | |
| Sum | 7 | 6 | 5 | 3 | 21 |

Consideration:

The bacterial vaginosis is a disease accompanied by the secretion of milk-like fluor giving out a bad smell and it has been discussed in relation to a variety of abnormalities observed in the perinatal period such as a high susceptibility to STD, the premature delivery and the premature rupture of membranes and in connection with the progress to pelvic inflammatory diseases (PID). It has been recognized that the bacterial vaginosis causes a significant decrease in the population of *Lactobacllus* spp. which plays an important role in the maintenance of the cleanliness in the vagina during the healthy condition and abnormal growth of anaerobic gram-negative *bacilli* such as *Prevotella* spp. (for instance, *P. melaninogenica* and *P. intermedia*) and *Bacteroides* spp.; anaerobic gram-positive *cocci* such as *P. anaerobius*; and further other microorganisms such as *G. vaginalis* and *Mycoplasma*. The group of these bacteria is referred to as the "bacterial vaginosis-related microorganism".

As has been described above, the *Sasa* extract can inhibit the growth of *Prevotella* spp. (for instance, *P. bivia*, *P. melaninogenica* and *P. intermedia*) at such a low concentration of 2%; the growth of *Bacteroides fragilis* group and *G. vaginalis* at a concentration of 6%. The foregoing investigation would make it clear that the *Sasa* extract can inhibit the growth of the whole strains of anaerobic cocci group examined herein at a concentration of 2%.

TEST EXAMPLE 16

Anti-microbial Activities of *Sasa* Extract against Bacterial Vaginosis-Related Microorganism As to *Mobiluncus* spp.

*Mobiluncus* spp. as an anaerobic gram-positive *bacillus* is an anaerobic asporogenic gram-positive anaerobic bacillus and belongs to the bacterial vaginosis-related microorganism which abnormally proliferate under the conditions of bacterial vaginosis (BV) characterized by the reduction of the intravaginal lactic acid bacteria, the reduction of the intravaginal pH and the milk-like fluor giving out a bad smell (an amine-like smell), along with *Prevotella bivia*, Pigmented *Prevotella* spp., *Porphyromonas* spp., *Mycoplasma genitalium* (hommnis) and *Gardnerella vaginalis*. In this Test Example, there were investigated the anti-microbial activities of the *Sasa* extract against bacteria of *Mobiluncus* spp.

Materials and Methods:

Strains Used: There were used 12 strains of *Mobiluncus* spp. These strains include *M. curtisii* subsp. *curtisii* ATCC 35242, *M. curtisii* subsp. *holmessii* ATCC 25241, *M. mullielis* ATCC 35240 and ATCC 35243. In addition, *Staphylococcus aureus* ATCC 25923 was also used as the MIC measurement precision-managing strain. The test solution used herein was the same as that used in Test Example 7.

Anti-microbial Activity Test: The minimum inhibitory concentration of the *Sasa* extract was determined according to the agar plate-dilution method used in the determination of the anti-microbial power of anti-microbial drugs. More specifically, there were prepared a series of *Brucella* HK blood-containing agar plates containing the *Sasa* extract at final concentrations of 8, 7, 6, 5, 4, 3, 2, 1, 0.5, 0.25 and 0.125%, respectively. The blood used herein was the sheep defibrinated blood (available from NISSEI Materials Co., Ltd.) lysed through freezing-thawing technique and it was added to the culture medium at a rate of 5%. The *Sasa* extract and the agar culture medium were mixed at a mixing ratio of 1:1 to thus form an agar culture medium containing a desired amount of the *Sasa* extract. In this connection, a 2N NaOH aqueous solution was used to adjust the pH value (pH: 7.0±0.3) of the culture medium.

The colony obtained by cultivating the test strain in a *Brucella* HK blood-containing agar culture medium (KY-OKUTO Pharmaceutical Co., Ltd.) over 72 hours was suspended in Anaerobe Broth MIC (available from Difco) to thus prepare a bacterial solution having a turbidity of Mc Farland #1 and a series of the *Sasa* extract-containing plates were inoculated with one platinum loop (10 µl) of the resulting bacterial solution according to the streak-smearing method. One platinum loop of the bacterial solution contains about $10^6$ bacterial cells under the present experimental conditions.

These samples were cultivated at 35° C. for two days in an anaerobic work station (available from GUNZE Industries, Inc.) and then the culture mediums were visually examined on whether each strain underwent growth or not. The case in which the strain underwent growth was judged to be positive (+).

Incidentally, the MIC values of the *Sasa* extract against *S. aureus* ATCC 25923 as determined under the experimental conditions used herein (pH 7.0) was found to be 8% (When comparing with the growth in the control culture medium, the concentration of the extract, at which the growth of the strain was significantly inhibited, was found to be 4%).

Results:

The results thus obtained are listed in the following Table 26. The *Sasa* extract could completely inhibit the growth of the strains of *Mobiluncus* spp. at a concentration of 4%. The MIC50% value thereof against *Mobiluncus* spp. was found to be 4%.

Consideration:

The bacterial vaginosis is a disease accompanied by the secretion of milk-like fluor giving out a bad smell and it has been discussed in relation to a variety of abnormalities observed in the perinatal period such as a high susceptibility to STD, the premature delivery and the premature rupture of membranes and in connection with the progress to pelvic inflammatory diseases (PID). It has been recognized that the bacterial vaginosis causes a significant decrease in the population of *Lactobacllus* spp. which plays an important role in the maintenance of the cleanliness in the vagina during the healthy condition and abnormal growth of anaerobic gram-negative *bacilli* such as *Prevotella* spp. (for instance, *P. melaninogenica* and *P. intermedia*) and *Bacteroides* spp.; anaerobic gram-positive *bacilli* such as *Mobiluncus* spp.; anaerobic gram-positive *cocci* such as *P. anaerobius*; and further other microorganisms such as *G. vaginalis* and *Mycoplasma*. The group of these bacteria is referred to as the "bacterial vaginosis-related microorganism". The inventors of this invention have confirmed in their studies that *Mobiluncus* spp. among the bacterial vaginosis-related microorganism includes bacterial strains which are detected at a high detection rate under the conditions whose BV score is high.

As has been described above, the *Sasa* extract can inhibit the growth of *Prevotella* spp. (for instance, *P. bivia, P. melaninogenica* and *P. intermedia*) at such a low concentration of 2%; the growth of *Bacteroides fragilis* group and *G. vaginalis* at a concentration of 6%; and the growth of the whole strains of anaerobic cocci group examined herein at a concentration of 2%. In this Test Example, the inventors have investigated *Mobiluncus* spp. Accordingly, the foregoing investigation could make it clear that the *Sasa* extract can inhibit the growth of these microorganisms at a concentration of 4%.

TABLE 26

Anti-microbial Activities of Sasa Extract Against *Mobiluncus* spp.

| Minimum Inhibitory Concn. of Sasa Extract (%) | Number of Strains |
|---|---|
| 8 | |
| 7 | |
| 6 | |
| 5 | |
| 4 | 6 |
| 3 | 2 |
| 2 | 4 |
| 1 | |
| 0.5 | |
| 0.25 | |
| 0.125 | |
| 0 | |
| Sum | 12 |

TEST EXAMPLE 17

Anti-microbial Activities of *Sasa* Extract against *Bacteroides Fragilis*

*Bacteroides fragilis* is an asporogenic anaerobic gram-negative *bacillus* isolated from human feces and it is a clinically quite important bacterial species in a variety of dermal infectious diseases and infectious diseases of subcutaneous soft tissues including, for instance, decubitus and periproctal abscess, along with *Staphylococcus aureus* URSA) and multiple drug-resistant *Pseudomonas aeruginosa*.

Strains Used: There were used 12 strains of *B. fragilis* in all. These strains were clinically isolated from patients suffering from a variety of purulent infectious diseases during the term beginning from January to July in 2002 and they have been stored in the present Facilities. *Escherichia coli* ATCC 25922 and *Staphylococcus aureus* ATCC 25923 were likewise used as the MIC measurement precision-managing strains. The test solution was the same as that used in Test Example 7.

Anti-microbial Activity Test: The minimum inhibitory concentration of the *Sasa* extract was determined according to the agar plate-dilution method used in the determination of the anti-microbial power of anti-microbial drugs. The determination was carried out according to the standard method as specified by the Chemotherapy Society of Japan. More specifically, there were prepared a series of variant GAM agar plates (available from NISSUI Pharmaceutical Co., Ltd.) containing the *Sasa* extract at final concentrations of 10, 9, 8, 7, 6, 5, 4, 3, 2, 1%, respectively. In his respect, the *Sasa* extract and the agar culture medium were mixed at a mixing ratio of 1:1 for the culture mediums having the *Sasa* extract concentration ranging from 10 to 6% and at a mixing ratio of 1:9 for the culture mediums having the *Sasa* extract concentration ranging from 5 to 1% to thus form agar culture mediums each containing a desired amount of the *Sasa* extract. In this connection, a 2N NaOH aqueous solution was used to adjust the pH value (pH: 6.6 to 7.1) of the culture mediums.

The colony obtained by cultivating the test strain in a *Brucella* HK blood containing agar culture medium (KY-OKUTO Pharmaceutical Co., Ltd.) over 48 hours was suspended in Anaerobe Broth MIC (available from Difco) to thus prepare a bacterial solution having a turbidity of Mc Farland #1 and a series of the *Sasa* extract containing plates were inoculated with one platinum loop (10 μl) of the resulting bacterial solution according to the streak-smearing method. One platinum loop of the bacterial solution contains bacterial cells of about $10^6$ cfu/ml under the present experimental conditions.

These samples were cultivated at 35° C. for one to two days in an anaerobic work station (available from GUNZE Industries, Inc.) and then the culture mediums were visually examined on whether each strain underwent growth or not. The case in which the strain underwent growth was judged to be positive (+).

Incidentally, the MC values of the *Sasa* extract against *E. coli* ATCC 25922 and *S. aureus* ATCC 25923 as determined under the experimental conditions used herein were both found to be 6%.

Results:

The MIC values of the *Sasa* extract against these 12 strains of *B. fragilis* were distributed within the range of from 4 to 6%. The MIC90% value thereof against the strains was found to be 5%.

TABLE 27

Anti-microbial Activities of Sasa Extract Against 12 Strains of *Bacteroides fragilis* Group

| Minimum Inhibitory Concn. of Sasa Extract (%) | Number of Strains |
|---|---|
| 10 | 0 |
| 9 | 0 |
| 8 | 0 |
| 7 | 0 |
| 6 | 1 |
| 5 | 10 |
| 4 | 1 |
| 3 | 0 |
| 2 | 0 |
| 1 | 0 |
| Total | 16 |

Consideration:

The bacteria of *Bacteroides fragilis* group (in particular, *B. fragilis*) are asporogenic anaerobic gram-negative anaerobic bacilli and naturally inhibit on the mucous membrane of the lower digestive tract. The bacterial cells of this bacterial group invade tissues and/or organs which are usually free of any baterium and cause infectious diseases when the mucous membrane is broken. These bacteria are anaerobic bacteria most frequently isolated from a variety of purulent infectious diseases, in particular purulent infectious diseases above the diaphragm and of the lower portions thereof This bacterium is present together with facultative *bacilli* such as *E. coli*, facultative and mircoaerophilic *cocci* such as staphylococci, enterococci and *Streptococcus milleri* group, and asporogenic anaerobic bacteria other than *Bacteroides*. In other words, This bacterium is important as one constituting multiple infectious diseases. Moreover, *B. fragilis* is natural resistant to a large number of anti-microbial drugs like a part of other facultative bacteria and the anti-microbial drugs showing an anti-microbial power are relatively limited and include, for instance, Clindamycins, Cephamycins and Carbapenems. However, they are apt to obtain an acquired resistance to these small number of anti-microbial drugs and this becomes a problem to be solved. For this reason, there is such a tendency that an anti-microbial drug having a wider spectrum or a plurality of anti-microbial drugs are used over a long period of time for the treatment of such infectious diseases in which the bacteria of *B. fragilis* are involved. However, the drug-resistant characteristics of not only the bacteria concerned, but also bacterial species other than this bacterium may further be increased depending on the method of using the same and therefore, these bacteria are quite troublesome bacterial species in the treatment of the infectious diseases.

The foregoing investigation makes it clear that the *Sasa* extract shows anti-microbial activities against the bacterial species of *B. fragilis* group as a typical bacterial group of the asporogenic anaerobic bacteria, which are important as causative bacteria of purulent multiple infectious diseases together with *S. aureus, P. aeruginosa* and *E. coli*, the anti-microbial activities being at least identical to those observed for the reference strains or *E. coli* and *S. aureus* as determined under the anaerobic conditions.

TEST EXAMPLE 18

Intrapelvic Infectious Diseases

The vagina of the healthy woman is a treasure-house of anaerobic and aerobic bacteria. Anaerobic bacteria are most predominantly present in the normal bacterial flora of the woman's birth canal and the density thereof is not less than 10 times that of the aerobic bacteria. The anaerobic bacteria comprise anaerobic gram-positive *cocci* and *Bacteroides* spp. (*Prevotella* spp. and *Bacteroides* spp. according to the present classification). The anaerobic bacteria are isolated from almost all of the patients suffering from infectious diseases of the birth canal in which any STD pathogen is not involved. Principal anaerobic pathogens include *Bacteroides fragilis, Prevotella bivia, Prevotella disiens, Prevotella melaninogenica*, anaerobic *cocci* and *Clostridium* spp. These anaerobic bacteria are involved in, for instance, ovaritubal abscess, septic abortion, intrapelvic abscess, endometritis and post-operative infectious diseases of wound sites, in particular, post-cesarean wound site-infectious diseases. In most of cases, these infectious diseases are multiple bacterial infectious diseases caused by anaerobic bacteria and Enterobacteriaceae, but there are observed infectious diseases caused by only anaerobic bacteria, in which any bacteria of the Enterobacteriaceae and other facultative bacteria are not isolated at all, in a higher frequency as compared with the intra-peritoneal infectious diseases. Moreover, these diseases are characterized by the excretion of bad smelling pus and blood out of the uterus, local tenderness on pressure of the lower abdominal region including the uterus or within the basin and continued fever and/or chill. The purulent thrombophlebitis of pelvic veins is sometimes complicated with these diseases and this may become a cause of the episode of recurrent septic pulmonary embolism.

The anaerobic bacteria have been considered to be factors relating to the etiological cause of the bacterial vaginosis. The syndromes, whose origin or factor has not yet been elucidated, are characterized by the effusive secretion giving out a bad smell and the abnormal increase of bacteria such as *Gardnerella vaginalis, Prevotella* spp., *Mobiluncus* spp. and *Peptostreptococcus* spp. as well as mycoplasmas within the vagina. It has been recognized that the anaerobic bacteria play an important role in the etiological cause of the intra-pelvic inflamatory diseases (PID) and some experts have reported the correlation between the bacterial vaginosis and the advance towards PID.

The intrapelvic infectious diseases caused by *Actinomyces* spp. are infectious diseases relating to the use of intra-uterine contraceptive appliances.

TEST EXAMPLE 19

Anti-microbial Activities of *Sasa* Extract against *Bifidobacterinum* spp.

When evaluating a substance showing an anti-microbial activity, it would be quite important to recognize, in advance, the effect of the substance on the human pathogenic bacteria as well as the effect thereof on the useful and opportunistic bacteria commonly present on the ski and/or mucous membranes.

Bacteria of *Bifidobacterium* spp. are known as the indigenous bacteria present in the digestive tracts and vaginae like those of *Lactobacllus* spp. and they are also known as useful bacteria free of any bacterial species whose pathogenic significance has never been indicated except for *Bifidobacterium dentium* which is known as a bacterium having pathogenicity against the respiratory organs. Thus, the inventors of this invention have investigated the anti-microbial activity of the *Sasa* extract against *Bifidobacterium* spp. using reference strains of *Bifidobacterium* spp.

Materials and Methods

Strain Used: There were used reference strains stored in the present Facilities and listed in the following Table 28 in this Test Example. These strains were purchased from ATCC and JCM and have been stored in this Facilities. Incidentally, control strains used herein were *Prevotella bivia* ATCC 29303, *Porphyromonas asaccharolytica* ATCC 25260, *Bacteroides fragilis* N-1, which were selected from the anaerobic bacteria most frequently isolated from patients suffering from infectious diseases in the fields of the gynecology and digestive tracts. In addition, *Escherichia coli* ATCC 25922 and *Staphylococcus aureus* ATCC 25923 were likewise used for the same purpose and as the precision-managing strains in the sensitivity-determination. The test solution was the same as that used in Test Example 7. Sterilized distilled water was used in the dilution of the solution.

Anti-microbial Activity Test: The minimum inhibitory concentration (MIC) of the *Sasa* extract was determined according to the agar plate dilution method used in the determination of the anti-microbial power of anti-microbial drugs. More specifically, there were prepared a series of variant GAM agar plates (available from NISSUI Pharmaceutical Co., Ltd) containing the *Sasa* extract at final concentrations of 9, 8, 7, 6, 5, 4, 3, 2, 1 and 0.5%, respectively. In his respect, the *Sasa* extract having a concentration ranging from 20 to 12% and the two-fold agar culture medium were mixed at a mixing ratio of 1:1 for the culture mediums having the *Sasa* extract concentration ranging from 10 to 6% and the *Sasa* extract having a concentration ranging from 50 to 5% and the one-fold agar culture medium were mixed at a mixing ratio of 1:9 for the culture mediums having the *Sasa* extract concentration ranging from 5 to 0.5% to thus form *Sasa* extract-containing agar culture mediums.

Preparation of Bacteral Solution for Inoculation:

The colony obtained by cultivating the test strain in a *Brucella* HK blood containing agar culture medium KYOKUTO Pharmaceutical Co., Ltd.) over 48 hours was scraped out with a cotton swab, suspended in Anaerobe Broth (available from Difco) to thus prepare a bacterial solution having a turbidity of Mc Farland No. 1 and a series of the *Sasa* extract-containing plates were inoculated with 10 µl (inoculum size: $10^6$ cfu/ml) each of the resulting bacterial solution according to the streak-smearing method. These samples were cultivated at 35° C. for 18 hours in an anaerobic work station (available from GUNZE Industries, Inc.) and then the culture mediums were visually examined on whether each strain underwent growth or not. The case in which the strain underwent growth was judged to be positive (+).

Results:

The following Table 28 shows the minimum inhibitory concentrations of the *Sasa* extract against these strains as determined under the acidic (pH 5.3 to 6.0) experimental conditions without adjusting the pH values of the culture mediums. The minimum inhibitory concentrations thereof observed for all of the strains (5 strains of 5 bacterial species) examined were found to be not less than 7%, except for one strains of *B. bifidum* whose MIC was found to be 4%. Moreover, the minimum inhibitory concentrations of the *Sasa* extract were found to be 0.5% for both *P. bivia* ATCC 29303 and *P. asaccharolytica* ATCC 25260 simultaneously examined herein and 4% for *E. coli* ATCC 25922 and *S. aureus* ATCC 25923 or the two AHSS precision-managing strains as determined according to this method.

Consideration:

It has been made clear that the *Sasa* extract can inhibit the growth of certain pathogenic bacteria at a concentration of not more than 6.25% (about 4% in most of cases). The inventors of this invention have considered that it is quite important to collect information concerning the anti-microbial activities of the *Sasa* extract against saprophytic bacteria, in addition to the anti-microbial power of the *Sasa* extract against these pathogenic bacteria, and have thus conducted the present investigation.

Most of *Lactobacllus* spp. and *Bifidobacterium* spp play important roles on the human mucous membranes from the viewpoint of the biological protection. The inventors of this invention have already reported that the *Sasa* extract shows anti-microbial activities against *L. crispatus* and *L. gasseri* belonging to the oxygen peroxide-producing *Lactobacllus* spp. in the order of not less than 10% (as expressed in terms of MIC) which is considerably weaker than those observed for typical pathogenic facultative bacteria such as *E. coli* and *S. aureus* (MIC: 4%) and those observed for typical purulent anaerobic bacteria such as *P. bivia, P. asaccharolytica* and *B. fragilis* (MIC: 0.5 to 4).

The foregoing results make it clear that the *Sasa* extract shows only weak anti-microbial activities against 5 strains of 5 bacterial species belonging to *Bifidobacterium* spp. naturally inhabiting in the intestinal tracts, as in the case of the *Lactobacllus* spp.

The foregoing results may intensely suggest that the anti-microbial activities of the *Sasa* extract against intravaginal useful bacteria and those present in the digestive tracts are relatively weaker than those observed for the opportunistic pathogenic bacteria.

TABLE 28

Anti-microbial Activities of Sasa Extract Against *Bifidobacterium* spp. Group

| Name of Bacteria | Minimum Inhibitory Concn. (%) Free of any pH-Control |
|---|---|
| *Bifidobacterium* | |
| *B. adolescentis* ATCC 15703 | 9 |
| *B. bifidum* JCM 1255 | 4 |
| *B. breve* ATCC 15700 | 7 |
| *B. longum* ATCC 15707 | 7 |
| *B. pseudolongum* ATCC 25526 | 8 |
| *Poprphyromonas* | |
| *P. asaccharolytica* ATCC 25260 | ≦0.5 |
| *Bacteroides* | |
| *B. fragilis* | 4 |
| *Escherichia coli* ATCC 25922 | 4 |
| *Staphylococcus aureus* ATCC 25923 | 4 |

*: Inoculum Size: One platinum loop of the bacterial solution having a turbidity of Mc Farland #1 was inoculated (1 cm) according to the streak-smearing method.

TEST EXAMPLE 20

Anti-Fungal Activities of *Sasa* Extract against *Candida albicans* and *Candida glabrata*

In this Test Example, there were investigated the anti-fungal activities of the *Sasa* extract against *Candida albicans* and *Candida glabrata* as the causative bacteria of "thrush", and vaginitis and vulvitis of women.

Strains Used: There were used 13 strains of *Candida albicans* and *Candida glabrata* in all. These strains are ones isolated from a variety of clinical materials in 2002 and stored in the present Facilities. In addition, there were also used *Escherichia coli* ATCC 25922, *Staphylococcus aureus* ATCC 25923, and *Pseudomonas aeruginosa* ATCC 27853 as the MIC precision-managing strains.

The test solution was the same as that used in Test Example 7. Sterilized distilled water was used in the dilution of the solution.

Anti-microbial Activity Test: The minimum inhibitory concentration of the *Sasa* extract was determined according to the agar plate-dilution method used in the determination of the anti-microbial power of anti-microbial drugs. More specifically, there were used a series of MH agar plates (available from Difco) containing the *Sasa* extract at final concentrations of 8, 7, 6, 5, 4, 3, 2 and 1%, respectively. In his respect, the *Sasa* extract and the agar culture medium were mixed at a mixing ratio of 1:9 to thus form *Sasa* extract-containing agar culture mediums each having a desired *Sasa* extract concentration. In this respect, a 2N NaOH aqueous solution or a 10% HCl aqueous solution was used for adjusting the pH value (2 kinds of pH values, i.e., about 7.0 and about 5.0) of the culture mediums.

The colony obtained by cultivating the test strain in a Micocell agar culture medium (BD) for 48 hours was suspended in MH Broth (available from Difco) to thus give a bacterial solution having a turbidity of McFarland #1 and a series of *Sasa* extract-containing plates were inoculated with one platinum loop (10 µl) of the bacterial suspension according to the streak-smearing method. One platinum loop of the bacterial solution contains about $10^6$ bacterial cells under the present experimental conditions.

These samples were cultivated at 35° C. for 24 hours and then the culture mediums were visually examined on whether each strain underwent growth or not. The case in which the strain underwent growth was judged to be positive (+).

Incidentally, the MIC values of the *Sasa* extract against *E. coli* ATCC 25922, *S. aureus* ATCC 25923 and *P. aeruginosa* ATCC 27853 as determined after one day under the present experimental conditions were found to be 2, ≦1 and 2 respectively at a pH value of 7 and all of them were found to be ≦1 at a pH value of 5. Moreover, the MIC values as determined at room temperature after 3 days were found to be 3, ≦1 and 3 at a pH value of 7 and 2, ≦1 and ≦1 at a pH value of 5.

Results:

The following Table 29 shows the distribution of minimum inhibitory concentrations of the *Sasa* extract against bacteria of *Candida* spp. as determined under the pH conditions of 5 and 7 after one day and 3 days. The data obtained at a pH value of 5 after 24 hours indicate that the *Sasa* extract can inhibit the growth of the whole strains or 8 strains of *C. albicans* and 4 strains of *C. glabrata* at a concentration of 5%. The data obtained after 3 days indicate that the concentration of the *Sasa* extract required for inhibiting the growth of the whole strains is 8%.

On the other hand, the data obtained at a pH value of 7 after 24 hours indicate that the *Sasa* extract can inhibit the growth of the whole. strains of *C. albicans*. The MIC for *C. glabrata* could not be evaluated The data obtained after 3 days indicate that not less than 8% of the *Sasa* extract was required for the complete inhibition of the whole strains including the strains of *C. glabrata*.

As the women's vaginitis, there have been known, for instance, vaginal trichomoniasis due to protozoa, mycotic vaginitis due to fungi, and bacterial vaginosis (or nonspecific vaginitis). The bacteria of *Candida* spp. as causative bacteria of vaginitis also serve as causative bacteria of vulvitis. The mycotic vaginitis is characterized by the secretion of cheese-like fluor unlike the other vaginitis and is a disease accompanied by quite strong urticant feeling. An anti-fungal agent is administered for the treatment of the same.

It has been confirmed from the investigation in this Test Example that the *Sasa* extract shows the growth-inhibitory effect on yeast-like fungi. The MIC values of the *Sasa* extract against these fungi as determined under acidic conditions after one day are distributed between 5% and 3%. Moreover, the MIC values as determined at a neutral pH established after the pH adjustment are distributed between 5% and 4%. When the MIC values were determined after allowing to stand at room temperature over 3 days, however, the MIC values of the *Sasa* extract against *Candida* spp. as determined at a pH of 5.0 were shifted from the range of from 5 to 3% to the range of from 7 to 4% for 12 strains except for one strain, for which the MIC value was 8%, and those observed at-a pH value of 7.0 were shifted from the range of from 5 to 4% to the level of not less than 8% for the whole 13 strains. This indicates that the *Sasa* extract exerts a bacteriostatic action on fungi at the MIC as determined after one day or higher extract concentrations and it suggests that the use of the *Sasa* extract at a higher concentration is required for the achievement of the bactericidal effect. Moreover, *C. glabrata* did not sufficiently grow when cultivating at 37° C. for one day in a neutral environment, but the *C. glabrata* sufficiently grew when it was allowed to stand at room temperature for 3 days and this permitted the determination of the MIC value. It was recognized that the *C. glabrata* sufficiently grew in an acidified Mueller Hinton culture medium even after the cultivation at 37° C. for one day and the MIC value thereof could thus be determined.

In the experiments carried out in this Test Example using the Mueller Hinton culture medium, it was found that the MIC values of the *Sasa* extract against *Candida* spp. fell within the range of from 7 to 4% and that the *Sasa* extract showed anti-microbial activities against these bacteria. The MIC value obtained under neutral conditions is about one-fole dilution higher than that observed in an acidic environment. Further, there was observed the growth of the bacteria of *Candida* spp. when allowing them to stand at room temperature even at a relatively higher concentration which could inhibit the growth of the bacteria when cultivating the same under neutral conditions for one day. This indicates that the action of the *Sasa* extract is bacteriostatic one. There was also observed the growth of the bacteria of *Candida* spp. under acidic conditions even at a concentration which could inhibit the growth of the bacteria when cultivating the same for one day, but the extend of the growth was lower than that observed in the neutral conditions. In other words, it has been made dear that the extract shows anti-microbial activity against *Candida* spp. under acidic conditions stronger than that observed for the bacteria under neutral conditions. When establishing the concentration of the *Sasa* extract for the clinical application thereof, it would be necessary to establish the concentration thereof to be used and the frequency of the use thereof while taking into consideration the foregoing fact in addition to the information concerning the toxicity of the *Sasa* extract.

The foregoing would strongly suggest that the *Sasa* extract showing an anti-fungal activity in addition to an anti-microbial activity can effectively be used as an agent for treating *Candida vaginitis* and vulvitis as well as other pathema in which *Candida* spp. is involved.

In addition, the inventors of this invention have recognized that the extract shows strong or medium anti-microbial activities against bacteria relating to the bacterial vaginosis such as *Prevotella* spp. and *Gardnerella vaginalis* and that it has other bacteriological characteristic properties and accordingly, the *Sasa* extract may have high usefulness as a therapeutic agent for the bacterial vaginosis. In this case, it may easily be predicted that the extract also showing an anti-fungal activity would naturally have an ability of preventing the occurrence of any bacterial exchange phenomenon or super-infection due to *Candida* spp., which has been reported as an epiphenomenon observed after the use of an anti-microbial drug completely free of any anti-fungal activity such as chloramphenicol presently used as a therapeutic agent for treating bacterial vaginosis.

TABLE 29

Anti-microbial Activities of Sasa extract Against *Candida albicans* and *Candida glaburata*; Influence of pH (5.0, 7.0) of Sensitivity-Measuring Culture Medium and Time (one day, 3 day) Elapsed till the Sensitivity is Determined

| Minimum Inhibitory Concn. (%) | Strains of *Candida albicans* | | | | Strains of *Candida glabrata* | | | |
|---|---|---|---|---|---|---|---|---|
| | pH5* | | pH7 | | pH5 | | pH7 | |
| | 1 day** | 3 days | 1 day | 3 days | 1 day | 3 days | 1 day | 3 days |
| >=8 | | 1 | | 8 | | | | 5 |
| 7 | | 4 | | | | | | |
| 6 | | 2 | | | | 4 | | |
| 5 | 1 | | 3 | | | 1 | | |
| 4 | 4 | 1 | 5 | | 4 | | | |
| 3 | 3 | | | | 1 | | | |
| 2 | | | | | | | | |
| 1 | | | | | | | | |
| ND*** | | | | | | | 5* | |
| Sum | 8 | 8 | 8 | 8 | 5 | 5 | 5 | 5 |

*The pH value of the culture medium;
**The time elapsed till the sensitivity is determined;
***Not determined
*The evaluation was deferred because of insufficient growth of the strain in the culture medium (pH 7.0) free of any Sasa extract

TEST EXAMPLE 21

Anti-microbial Activities of *Sasa* Extract against *Staphylococcus* spp. Derived from Lesions of Patients Suffering from *Acne Vulgaris*

The *Sasa* extract can completely inhibit the growth of *Propionibacterium acnes* which is important as one of etiological factors of acne (*Acne vulgaris*) at a concentration of 6.25%. Moreover, it was also proved that the *Sasa* extract could completely inhibit the growth of *Staphylococcus aureus* (MRSA) important as a purulent coccus at a concentration of not more than 1%. The inventors of this invention have thus investigated the anti-microbial activities of the *Sasa* extract using 14 strains of *Staphylococcus* spp. in all isolated from the lesions of patients suffering from *acne* and important as the exacerbation factors of *acne*, which comprises 13 strains of *Staphylococcus epidermidis* and one strain of *Staphylococcus cohnii*, according to the agar plate-dilution method.

Materials and Methods

Strains Used: There were used 14 strains in all comprising 13 strains of *Staphylococcus epidermidis* and one strain of *Staphylococcus cohnii*. In addition, *Escherichia coli* ATCC 25922 and *S. aureus* ATCC 25923 were also used as the sensitivity-determining precision-managing strains. The following Table 30 shows the bacterial species of the strains used and the anti-microbial drug-sensitivity pattern thereof.

TABLE 30

Anti-microbial Drug-Resistance Pattern of *Staphylococcus* spp. Derived from Lesions of Acne

| No. of Strain | Bacterial Species | Sensitivity Pattern (TC, CLDM, OFLX) |
|---|---|---|
| N-4 | *S. epidermidis* | $TC^R$, |
| N-5 | *S. epidermidis* | |
| N-6 | *S. epidermidis* | $CLDM^R$ |
| N-7 | *S. epidermidis* | |
| N-8 | *S. epidermidis* | |
| N-15 | *S. epidermidis* | $TC^R$ |
| N-26 | *S. epidermidis* | |
| N-39 | *S. epidermidis* | |
| N-34 | *S. epidermidis* | $OFLX^R$ |
| N-37 | *S. epidermidis* | $TC^R$, $CLDM^R$ |
| N-38 | *S. epidermidis* | |
| N-46 | *S. epidermidis* | |
| N-48 | *S. cohnii* | $TC^R$, $CLDM^R$ |
| N-68 | *S. epidermidis* | |

The test solution was the same as that used in Test Example 7. Sterilized distilled water was used in the dilution of the solution.

Anti-microbial Activity Test: The minimum inhibitory concentration (MIC) of each sample was determined according to the agar plate-dilution method used in the determination of the anti-microbial power of anti-microbial drugs against facultative bacteria. More specifically, the measurement was carried out according to the standard technique specified in the Chemotherapy Society of Japan, as much as possible. A series of Mueller Hinton agar plates (available from Difco) each containing the *Sasa* extract were prepared in such a manner that the final concentrations of the extract were equal to 5, 4, 3, 2, 1, 0.5, 0.25 and 0.125%, respectively. The *Sasa* extract having a concentration ranging from 50% to 1.25% and the Mueller Hinton culture medium of one-fold concentration were admixed together in a mixing ratio of 1:9 to thus form a *Sasa* extract-containing agar culture medium. The pH values of the culture mediums were controlled to a level of 6.1 to 7.1 with a 2N NaOH aqueous solution. The MIC values of the *Sasa* extract against *S. aureus* ATCC 25922 and *E. coli* ATCC 25922 were both found to be 2%.

Preparation of Bacteria-Containing Solution for Inoculation and Evaluation:

The colony of the test strain obtained by cultivating it on TSA agar culture medium over 24 to 48 hours was scraped out with a sterilized cotton swab and suspended in Mueller Hinton broth (available from Difco) to thus form a bacteria-containing solution having a turbidity of Mc Farland No. 1. The resulting bacteria-containing solution (10 μl) was suspended in 1 ml of Mueller Hinton broth and 10 μl each of the resulting suspension was inoculated in the series of the *Sasa* extract-containing plates according to the streak-smearing method. After cultivating these culture medium inoculated at 35° C. for 20 hours in an aerobic environment and the culture mediums were visually examined on whether each strain underwent growth or not.

Results:

The anti-microbial activities of the *Sasa* extract were investigated using 14 strains of *Staphylococcus* spp. in all comprising 13 strains of *Staphylococcus epidermidis* and one strain of *Staphylococcus cohnii* according to the agar plate dilution method. As a result, the *Sasa* extract completely inhibited the growth of these strains at a concentration of 1%.

Regarding these 14 strains, they were inspected for the sensitivity to three anti-microbial drugs (Tetracycline, Clindamycin and Ofloxacin) and these strains include two strains having single drug-resistance to Tetracycline, one strain having single drug-resistance to Clindamycin, two strains having two drug-resistance to Tetracycline and Clindamycin and one strain having drug-resistance to Ofloxacin, but the *Sasa* extract equally inhibited the growth of these drug-resistant strains at a concentration of not more than 1%.

TABLE 31

Anti-microbial Action of Sasa Extract Against 14 Strains of *Staphylococcus* spp.

| Growth-Inhibitory Concn. (%) | Drug-sensitive | Drug-resistant | Total |
|---|---|---|---|
| 5 | | | |
| 4 | | | |
| 3 | | | |
| 2 | 3 | | 3 |
| 1 | 4 | 4 | 8 |
| 0.5 | 1 | 2 | 3 |
| 0.25 | | | |
| 0.125 | | | |
| Sum | 8 | 6 | 14 |

Consideration:

The inventors of this invention investigated the sensitivity, to the *Sasa* of 14 strains of *Staphylococcus* spp. in all comprising 13 strains of *Staphylococcus epidermidis* and one strain of *Staphylococcus cohnii* isolated from patients suffering from acne and important as exacerbation factors of the acne, according to the agar plate-dilution method. As a result, it was found that the *Sasa* extract completely inhibited the growth of these strains at a concentration of 2%. The 14 strains which had been subjected to tests for examining the sensitivities to three anti-microbial drugs (Tetracycline, Clindamycin and Ofloxacin) included two strains having single drug-resistance to Tetracycline, one strain having single drug-resistance to Clindamycin, two strains having two drug-resistance to Tetracycline and Clindamycin and one strain having single drug-resistance to Ofloxacin, but the *Sasa* extract equally inhibited the growth of these drug-resistant strains at a concentration of not more than 2%.

The foregoing facts would suggest that the *Sasa* extract the *Sasa* extract also shows sufficient activities against *Staphylococcus* spp. as the exacerbation factors so long as the concentration of the extract is 6.25% which permits the inhibition of the growth of *P. acnes* and the extract can thus be quite effective as an agent for treating *acne*.

TEST EXAMPLE 22

Anti-microbial Activities of *Sasa* Extract against *Staphylococcus* spp. Derived from Lesions of Patients Suffering from *Acne Vulgaris*

In this Test Example, the inventors investigated the anti-microbial activities of the *Sasa* extract against 44 strains, in total, of *Staphylococcus epidermidis* spp. isolated from the lesions of patients suffering from *acne*, according to the agar plate-dilution method.

Strains Used: There were used 44 strains of *Staphylococcus* spp. In addition, *Escherichia coli* ATCC 25922 and *S. aureus* ATCC 25923 were also used as the sensitivity-determining precision-managing strains. The test solution was the same as that used in Test Example 7. Sterilized distilled water was used in the dilution of the solution.

Anti-microbial Activity Test: The minimum inhibitory concentration (MIC) of each sample was determined according to the agar plate-dilution method used in the determination of the anti-microbial power of anti-microbial drugs against facultative bacteria. More specifically, the measurement was carried out according to the standard technique specified in the Chemotherapy Society of Japan, as much as possible. A series of Mueller Hinton agar plates (available from Difco) each containing the *Sasa* extract were prepared in such a manner that the final concentrations of the extract were equal to 5, 4, 3, 2, 1, 0.5, 0.25 and 0.125%, respectively. The pH values of the culture mediums were controlled to a level of 6.1 to 7.1 with a 2N NaOH aqueous solution. The MIC values of the *Sasa* extract against *S. aureus* ATCC 25922 and *E. coli* ATCC 25922 were both found to be 2%.

Preparation of Bacteria-Containing Solution for Inoculation and Evaluation:

The colony of the test strain obtained by cultivating it on TSA agar culture medium over 24 to 48 hours was scraped out with a sterilized cotton swab and suspended in Mueller Hinton broth (available from Difco) to thus form a bacteria-containing solution having a turbidity of Mc Farland No. 1. The resulting bacteria-containing solution (10 µl) was suspended in 1 ml of Mueller Hinton broth and 10 µl each of the resulting suspension was inoculated in the series of the *Sasa* extract-containing plates according to the streak-smearing method. After cultivating these culture medium inoculated at 35° C. for 20 hours in an aerobic environment and the culture mediums were visually examined on whether each strain underwent growth or not. The results thus obtained are summarized in the following Table 32.

TABLE 32

Sensitivities of *Staphylococcus* spp. (44 Strains) to Sasa Extract and Various Kinds of Anti-microbial Drugs

| Drug | MIC50(µg/ml) | MC80(µg/ml) | MIC Range(µg/ml) |
|---|---|---|---|
| Nadifloxacin | 0.05 | 0.78 | 25~0.025 |
| Ofloxacin | 0.39 | 0.78 | >100~0.19 |
| Minocycline | 0.10 | 0.10 | 50~0.10 |
| Tetracycline | 0.39 | 25 | >100~0.19 |
| Clindamycin | 0.10 | >100 | >100~0.025 |
| Extract | MIC50(%) | MIC80(%) | MIC Range (%) |
| Sasa extract | 0.5% | 1% | 2~0.125% |

1) *Staphylococcus epidermidis*: 34 strains,
*S. capitis*: 2 strains,
*S. aureus*: 2 strains,
*S. cohnii*: 1 strain,
*S. hominis*: 1 strain,
*S. haemolyticus*: 1 strain,
*Staphylococcus* sp.: 3 strains.

TEST EXAMPLE 23

Anti-microbial Activities of *Sasa* Extract against Vaginitis and Bacterial Vaginosis-Related Microorganisms The test solution was the same as that used in Test Example 7. This is a brown, acidic and slightly viscous liquid having a concentration of 50% (w/v) and giving out fragrance.

Method for Examining Anti-microbial Power: The minimum inhibitory concentration (MIC) of the *Sasa* extract for each sample was determined using a variant GAM agar culture medium or a *Brucella* HK agar culture medium as a basic culture medium for the determination according to the method for the determination of the anti-microbial power of anti-microbial drugs against the anaerobic bacteria.

Strains Used in These Test: There were used herein *Candida* spp. and *Prevotella bivia* (14 strains); Pigmented *Prevotella* spp. (9 strains); bacteria of anaerobic cocci group or *Finegoldia, Micromonas, Peptostreptococcus* (21 strains); *Mobiluncus* spp. (12 strains); and *Gardnerella vaginalis* (11 strains).

Results and Summary:

Thus, there have been made clear the degrees of the anti-microbial activities of the *Sasa* extract against the facultative anaerobic and anaerobic bacteria and *Candida* spp. as the BV-related microorganisms. More specifically, the *Sasa* extract could inhibit the growth of *Candida* spp. at a concentration ranging from 3 to 5%; the growth of *G. vaginalis* at a concentration of 6%; the growth of *Mobiluncus* spp. at a concentration of 4%; the growth of anaerobic cocci at a concentration of 3%; and the growth of *Prevotella* spp. at a concentration of 1%.

TEST EXAMPLE 24

Anti-microbial Spectra of *Sasa* Extract against Obligatory Anaerobic Bacteria

The anti-microbial spectra of the *Sasa* extract was investigated at a pH value of 6.0 and 7.0 using reference strains of anaerobicbacteria.

In this Test Example, there were investigated the anti-microbial actions of the *Sasa* extract under neutral conditions (pH: about 7.0) and weakly acidic conditions (pH: about 6.0) using a large number of strains of the laboratory-stored obligatory anaerobicbacteria including a part of microaerophilic bacteria, which are hard to handle, and facultative bacteria (such as *Streptococcus, Lactobacllus, Actinomyces, Sutterella*), for the purpose of making the anti-microbial spectra of the *Sasa* extract clear.

Stains Used:

There were used reference strains stored in the present Facilities (see, The following Tables 33 to 36). *Escherichia coli* ATCC 25922 and *Staphylococcus aureus* ATCC 25923 were likewise used as the MIC precision-managing strains. The test solution was the same as that used in Test Example 7. Sterilized distilled water was used in the dilution of the solution.

Anti-microbial Activity-Determining Test:

The minimum inhibitory concentration of the *Sasa* extract was determined according to the agar plate-dilution method used in the determination of the anti-microbial power of anti-microbial drugs. More specifically, there were prepared a series of variant GAM agar plates (available from NISSUI Pharmaceutical Co., Ltd.) containing the *Sasa* extract at final concentrations of 6.4, 3.2, 1.6, 0.8, 0.4, 0.2, 0.1%, respectively. In this connection, a 2N NaOH aqueous solution or a 10% hydrochloric acid aqueous solution was used to adjust the pH value of the culture mediums and the target pH values thereof were set at 6.0 and 7.0.

The colony obtained by cultivating the test strain in a *Brucella* HK blood-containing agar culture medium (KYOKUTO Pharmaceutical Co., Ltd.) over 48 hours was suspended in Anaerobe Broth MIC (available from Difco) to thus prepare a bacterial solution having a turbidity of Mc Farland #1, followed by the dilution thereof 10 times and a series of the *Sasa* extract-containing plates were inoculated with one platinum loop of the resulting diluted bacterial solution according to the streak smearing method One platinum loop of the bacterial solution contains about $10^4$ bacterial cells under the present experimental conditions.

These samples were cultivated at 35° C. for two days (for one day, in case of the *Clostridium*) in an anaerobicwork station (available from GUNZE Industries, Inc.) and then the culture mediums were visually examined on whether each strain underwent growth or not. The case in which the strain underwent growth was judged to be positive (+). The results thus obtained are summarized in the following Tables 33 to 36.

TABLE 33

Anti-microbial Powers of Sasa Extract Against 1)
Aerobic Cocci (*Peptostreptococcus, Staphylococcus, Finegoldia, Micromonas, Atopobium, Gemella*);
and Microaerophilic Bacteria (*Streptococcus*);
Anaerobic Gram-Positive Bacilli (*Actinomyces, Eubacterium, Propionibacterium, Bifidobacterium*)

| Name of Bacteria | pH 7.2 +/− 0.2 | pH 5.8 +/− 0.2 |
|---|---|---|
| *Peptostreptococcus anaerobius* ATCC27337 | 0.4 | ND |
| *Peptostreptococcus asaccharolyticus* WAL3218 | 0.4 | ND |
| *Peptostreptococcus indolicus* GAI0915 | 1.6 | ND |
| *Peptostreptococcus prevotii* ATCC9321 | 3.2 | ND |
| *Micromonas micros* VPI-5464-1 | 1.6 | ND |
| *Finegoldia magna* ATCC29328 | 1.6 | ND |
| *Staphylococcus saccharolyticus* ATCC14953 | 0.8 | ND |
| *Streptococcus intermedius* ATCC27823 | >6.5 | 3.2 |
| *Streptococcus constellatus* ATCC27735 | >6.5 | 3.2 |
| *Atopobium parvulum* VPI0546 | 1.6 | ND |
| *Gemella morbillorum* ATCC27824 | 3.2 | 1.6 |
| *Propionibacterium acnes* ATCC11828 | 6.5 | 6.5 |
| *Propionibacterium granulosum* ATCC25564 | 6.5 | 6.5 |
| *Eggerthella lenta* ATCC25559 | >6.5 | 6.5 |
| *Actinomyces odontolyticus* GAI-91002 | >6.5 | 6.5 |
| *Bifidobacterium adolescentis* ATCC15703 | >6.5 | 1.6 |
| *Bifidobacterium bifidum* JCM1255 | 6.5 | ND |
| *Bifidobacterium breve* ATCC15700 | 6.5 | 6.5 |
| *Bifidobacterium longum* ATCC15707 | >6.5 | 6.5 |
| *Bifidobacterium pseudolongum* ATCC25526 | >6.5 | 6.5 |
| *Bacteroides fragilis* ATCC25285 | 6.5 | 3.2 |
| *Bacteroides thetaiotaomicron* ATCC29741 | 6.5 | 6.5 |

TABLE 33-continued

Anti-microbial Powers of Sasa Extract Against 1) *Aerobic Cocci* (*Peptostreptococcus, Staphylococcus, Finegoldia, Micromonas, Atopobium, Gemella*); and Microaerophilic Bacteria (*Streptococcus*); Anaerobic Gram-Positive Bacilli (*Actinomyces, Eubacterium, Propionibacterium, Bifidobacterium*)

| Name of Bacteria | pH 7.2 +/− 0.2 | pH 5.8 +/− 0.2 |
| --- | --- | --- |
| *Escherichia coli* ATCC25922 | >6.5 | 6.5 |
| *Staphylococcus aureus* ATCC25923 | 6.5 | 1.6 |

Inoculum Size: $10^8$ cells/ml;
Cultivation Time for Evaluation: 48 hours.
Note:
The following strains did not grow at a pH value of 6.0: *Peptostreptococcus anaerobius* ATCC 27337, *Peptostreptococcus asaccharolyticus* WAL 3218, *Peptostreptococcus indolicus* GAI 0915,*Peptostreptococcus prevotii* ATCC 9321, *Micromonas micros* VPI-5464-1, *Finegoldia magna* ATCC 29328, *Staphylococcus saccharolyticus* ATCC 14953, *Atopobium parvulum* VPI 0546, *Bifidobacterium bifidum* JCM 1255.

TABLE 34

Anti-microbial Actions of Sasa Extract Against Lactobacilli (*Lactobacillus*) and Anaerobic Gram-Negative Bacilli (*Bacteroides*)

| Name of Bacteria | pH 7.1 +/− 0.3 | pH 5.8 +/− 0.3 |
| --- | --- | --- |
| *Lactobacillus acidophilus* JCM1132 | >6.5 | >6.5 |
| *Lactobacillus brevis* ss. *brevis* JCM1059 | >6.5 | >6.5 |
| *Lactobacillus casei* ss. *casei* JCM1134 | >6.5 | >6.5 |
| *Lactobacillus plantarum* JCM1173 | >6.5 | >6.5 |
| *Lactobacillus reuteri* JCM1149 | >6.5 | >6.5 |
| *Lactobacillus salivarius* ss. *salivarius* JCM1112 | >6.5 | >6.5 |
| *Bacteroides fragilis* GAI5562 | 6.5 | 6.5 |
| *Bacteroides fragilis* ATCC25285 | 6.5 | 6.5 |
| *Bacteroides fragilis* NCTC10581 | 6.5 | 3.2 |
| *Bacteroides fragilis* GAI-0558 Penicillin-resistance | 6.5 | 6.5 |
| *Bacteroides fragilis* GAI-7955 Penicillin-resistance | 6.5 | 3.2 |
| *Bacteroides fragilis* GAI-10150 Penicillin-resistance | 6.5 | 6.5 |
| *Bacteroides fragilis* GAI30079 Carbapenem-resistance | 6.5 | 6.5 |
| *Bacteroides fragilis* GAI30144 Carbapenem-resistance | 6.5 | 6.5 |
| *Bacteroides vulgatus* ATCC8482 | 6.5 | 3.2 |
| *Bacteroides distasonis* ATCC8503 | 6.5 | 3.2 |
| *Bacteroides ovatus* ATCC8483 | 6.5 | 6.5 |
| *Bacteroides thetaiotaomicron* ATCC29741 | 3.2 | 6.5 |
| *Bacteroides uniformis* ATCC8482 | 3.2 | 3.2 |

Inoculum Size: $10^7$ cells/ml;
Cultivation Time for Evaluation: 48 hours at 35° C.

TABLE 35

Anti-microbial Actions of Sasa Extract Against Anaerobic Gram-Negative Bacilli (*Bacteroides, Prevotella, Porphyromonas, Fusobacterium, Bilophila, Desulfovibrio*); Microaerophilic Bacteria (*Campylobacter, Sutterella,Capnocytophaga*); and Anaerobic Gram-Negative Cocci (*Veillonella*)

| Name of Bacteria | pH 7.0 +/− 0.2 | pH 6.0 +/− 0.2 |
| --- | --- | --- |
| *Bacteroides eggerthii* ATCC 27754 | 1.6 | 3.2 |
| *Bacteroides ureolyticus* NCTC 10941 | 0.8 | 0.8 |
| *Campylobacter gracilis* JCM 8538 | 3.2 | 3.2 |
| *Sutterella wadsworthensis* ATCC 51579 | 6.5 | 6.5 |
| *Prevotella bivia* ATCC 29303 | 0.4 | 0.8 |
| *Prevotella buccae* ATCC 33574 | 0.8 | 1.6 |
| *Prevotella corporis* GAI 91000 | 0.4 | 0.8 |
| *Prevotella heparinolytica* ATCC 35895 | 0.4 | ND |
| *Prevotella intermedia* ATCC 25611 | 0.8 | 1.6 |
| *Prevotella melaninogenica* GAI 5490 | 3.2 | 3.2 |
| *Prevotella oralis* ATCC 33269 | 1.6 | 3.2 |
| *Prevotella oris* ATCC 33573 | 0.4 | 0.8 |
| *Porphyromonas asaccharolytica* ATCC 25260 | 0.2 | ND |
| *Porphyromonas gingivalis* ATCC 33277 | 0.4 | ND |
| *Fusobacterium nucleatum* ATCC 25586 | 1.6 | 1.6 |
| *Fusobacterium varium* ATCC 8501 | 1.6 | 3.2 |
| *Fusobacterium necrophorum* ATCC 25286 | 0.8 | 0.8 |
| *Bilophila wadsworthia* WAL 7959 | 0.2 | ND |
| *Desulfovibrio piger* DSM 749 | 0.4 | ND |
| *Veillonella parvula* ATCC 10790 | 0.8 | 1.6 |
| *Veillonella dispar* ATCC 17748 | 0.8 | 1.6 |
| *Capnocytophaga ochracea* GAI-5586 | 1.6 | 0.4 |
| *Bacteroides fragilis* ATCC 25285 | 6.5 | 6.5 |
| *Bacteroides thetaiotaomicron* ATCC 29741 | 3.2 | 6.5 |

Inoculum Size: $10^7$ cells/ml;
Cultivation Time for Evaluation: 48 hours at 35° C.
Note:
The following strains did not grow in the control culture mediums of pH 6.0 and free of any Sasa extract: *Prevotella heparinolytica* ATCC 35895, *Porphyromonas asaccharolytica* ATCC 25260, *Porphyromonas gingivalis* ATCC 33277, *Bilophila wadsworthia* WAL 7959, *Desulfovibrio piger* DSM 749.

TABLE 36

Anti-microbial Activities of Sasa Extract Against Sporangial Anaerobic Bacteria (*Clostridium*)

| Name of Bacteria | pH 7.0 +/- 0.3 | pH 6.0 +/- 0.3 |
|---|---|---|
| *Clostridium difficile* GAI 10029 | 1.6 | 0.4 |
| *Clostridium sordellii* ATCC 9714* | 6.5 | .1.6 |
| *Clostridium septicum* ATCC 12464* | 3.2 | 1.6 |
| *Clostridium perfringens* ATCC 13124* | 3.2 | 1.6 |
| *Clostridium ramosum* ATCC 25582 | 1.6 | 0.8 |
| *Clostridium clostridiiforme* NCTC 11224 | 0.8 | 0.8 |
| *Bacteroides fragilis* ATCC 25285 | 3.2(24 Hr) | 3.2(24 hr) |
| *Bacteroides thetaiotaomicron* ATCC 29741 | 3.2(24 hr) | 3.2(24 hr) |

*Clostridium septicum, Clostridium sordellii, Clostridium perfringens* belong to the group of gas gangrene-inducing bacteria.
Inoculum Size: $10^7$ cells/ml;
Cultivation Time for Evaluation: 24 hours at 35° C.

Summary

The outline of the anti-microbial spectra of the *Sasa* extract against the anaerobic bacteria group has thus been made clear. If it is assumed that the *Sasa* extract shows a strong anti-microbial power when the MIC value thereof is not more than 3%; a medium anti-microbial power when the MIC value thereof ranges from 4 to 6%; and a weak anti-microbial power when the MIC value thereof is not less than 7%, the inventors can conclude as follows:

The *Sasa* extract showed a strong anti-microbial power against asporogenic anaerobic gram-positive *cocci* (*Finegoldia, Micromonas, Peptostreptococcus, Atopobium*, and *Gemella*). However, the *Sasa* extract showed only a weak anti-microbial power against anginosus group as microaerophilic bacteria.

Regarding the asporogenic gram-positive anaerobic bacteria, the *Sasa* extract showed a medium anti-microbial power against *Propionibacterium*; a weak anti-microbial power against *Actinomyces, Bifidobacterium* and *Lactobacllus*. Regarding the asporogenic anaerobic gram-negative *bacilli*, the *Sasa* extract showed a strong anti-microbial power against *Prevotella, Porphyromonas, Bilophila, Desulfovivrio* and *Fusobacterium*; and a medium anti-microbial power against *Bacteroides* and *Sutterella*. Moreover, the extract showed a strong anti-microbial power against anaerobic gram-negative *cocci* (*Veillonella*). In addition, with respect to *Clostridium*, the extract showed a strong anti-microbial power against all of the strains except for *C. sordellii* for which it showed a medium anti-microbial power.

INDUSTRIAL APPLICABILITY

The anti-microbial agent of the present invention shows strong anti-microbial actions against *Clostridium tetani*, *Candida* spp. (such as *Candida albicans* and *Candida glabrata*), bacteria of the genus *Propionibacterium*, gas gangrene-inducing bacteria, various kinds of resistant bacteria (such as Methicillin-resistant *Staphylococcus aureus*) and vaginitis and vaginosis-related microorganisms (such as *Finegoldia, Micromonas* and *Peptostreptococcus*); shows weak anti-microbial actions against *Actinomyces, Bifidobacterium* and *Lactobacllus*; and also shows anti-viral actions against viruses such as herpes virus. Accordingly, the anti-microbial agent is effectively used in, for instance, anti-microbial ink, anti-microbial paints and varnishes, anti-microbial sake, anti-microbial adhesives, anti-microbial beverages, anti-microbial foods, anti-microbial seasonings, anti-microbial agents for animals or plants, preservatives, an agricultural disinfectant and agricultural chemicals. In particular, the anti-microbial agent of the present invention shows particularly high anti-microbial actions when it comprises an organic acid (such as malic acid) in addition to the *Sasa* extract.

What is claimed is:

1. A method for inhibiting growth of at least one microorganism selected from *Propionibacterium* comprising the steps of providing an anti-microbial agent comprising *Sasa* extract in an amount ranging from 1 to 50% by mass as expressed in terms of a solid content of the anti-microbial agent and contacting the microorganism to the anti-microbial agent,
   wherein the anti-microbial agent comprises an organic acid in an amount of from 0.01 to 5% by mass based on the total mass of the anti-microbial agent and said organic acid is selected from the group consisting of malic acid, citric acid, lactic acid, oxalic acid, malonic acid, succinic acid, fumaric acid, acetic acid, benzoic acid, phenyl-acetic acid, salicylic acid and phenols, and
   wherein the *Sasa* extract is prepared by extracting raw leaves or dried leaves of *Sasa* with water maintained at a temperature ranging from 100 to 180° C. at ordinary pressure or while applying a pressure, or
   wherein the *Sasa* extract is prepared by extracting leaves of *Sasa albo-marginata* in a first extraction at a temperature ranging from 100 to 180° C. for 5 to 30 minutes using a pressurized hot water extraction device to obtain a first extract, separating the first extract from a moisture-containing solid content in a moisture separator, treating the moisture-containing solid content at a temperature ranging from 100 to 200° C. for 5 to 60 minutes in a saturated vapor-heating device, further treating the solid content thus treated in a second extraction at 100 to 180° C. for 5 to 30 minutes using a pressurized hot water extraction device to obtain a second extract and combining the extracts obtained in the first and second extraction steps, or
   wherein the *Sasa* extract is prepared by extracting dried leaves of *Sasa albo-marginata* with water heated to 60 to 100° C. for 30 minutes to 12 hours.

2. The method as set forth in claim 1, wherein the microorganism is *Propionibacterium acnes*.

3. The method as set forth in claim 1, wherein the organic acid is malic acid.

4. The method as set forth in claim 1, wherein the anti-microbial agent comprises *Sasa* extract in an amount ranging from 2 to 25% by mass as expressed in terms of the solid content of the anti-microbial agent and the organic acid in an amount of from 0.02 to 3% by mass based on the total mass of the anti-microbial agent.

5. The method as set forth in claim 1, wherein the anti-microbial agent comprises *Sasa* extract in an amount ranging from 4 to 15% by mass as expressed in terms of the solid content of the anti-microbial agent and the organic acid in an amount of from 0.05 to 1.5% by mass based on the total mass of the anti-microbial agent.

6. The method as set forth in claim 4, wherein the organic acid is malic acid.

7. The method as set forth in claim 5, wherein the organic acid is malic acid.

* * * * *